US012685750B2

(12) United States Patent
Chen et al.

(10) Patent No.: US 12,685,750 B2
(45) Date of Patent: Jul. 21, 2026

(54) CHIMERIC ANTIGEN RECEPTOR WITH MODIFIED HINGE REGION AND USES THEREOF

(71) Applicants: Orgenesis Inc., Germantown, MD (US); Broaden BioScience and Technology Corp., Katy, TX (US)

(72) Inventors: Buo Chen, Katy, TX (US); Xiangqun Li, Beijing (CN); Ang Zhang, Beijing (CN)

(73) Assignee: BROADEN BIOSCIENCE AND TECHNOLOGY CORP, Katy, TX (US)

( * ) Notice: Subject to any disclaimer, the term of this patent is extended or adjusted under 35 U.S.C. 154(b) by 264 days.

(21) Appl. No.: 18/050,461

(22) Filed: Oct. 27, 2022

(65) Prior Publication Data

US 2023/0381230 A1    Nov. 30, 2023

Related U.S. Application Data

(60) Provisional application No. 63/272,617, filed on Oct. 27, 2021.

(51) Int. Cl.
| | |
|---|---|
| *A61K 35/17* | (2015.01) |
| *A61K 40/31* | (2025.01) |
| *C07K 14/705* | (2006.01) |
| *C12N 5/0783* | (2010.01) |

(52) U.S. Cl.
CPC .............. *A61K 35/17* (2013.01); *A61K 40/31* (2025.01); *C07K 14/70503* (2013.01); *C12N 5/0636* (2013.01); *C07K 2317/53* (2013.01); *C07K 2317/565* (2013.01); *C07K 2317/622* (2013.01)

(58) Field of Classification Search
CPC . A61K 40/31; A61K 2239/17; C07K 2317/53
See application file for complete search history.

(56) References Cited

U.S. PATENT DOCUMENTS

| | | | | |
|---|---|---|---|---|
| 2013/0287748 | A1* | 10/2013 | June ................... | C07K 16/3061 435/328 |
| 2015/0031624 | A1* | 1/2015 | Feldman .......... | C07K 14/70517 435/7.1 |
| 2024/0043803 | A1* | 2/2024 | Deuse .............. | C07K 14/70535 |

FOREIGN PATENT DOCUMENTS

| | | | | |
|---|---|---|---|---|
| WO | WO-2022125439 A2 * | 6/2022 | .............. | A61P 35/00 |

OTHER PUBLICATIONS

Ang Zhang et al, "Reducing Hinge Flexibility of CAR-T Cells Prolongs Survival In Vivo With Low Cytokines Release", Oct. 5, 2021, Frontiers in Immunology, 12:724211. (Year: 2021).*
Alabanza et al Mol. Therapy 25:11 2452 (Year: 2017).*

* cited by examiner

*Primary Examiner* — Daniel E Kolker
(74) *Attorney, Agent, or Firm* — Mark S. Cohen; PEARL COHEN LLP

(57) ABSTRACT

The present disclosure provides a chimeric antigen receptor (CAR) molecule comprising a modified hinge domain, wherein the hinge domain comprises the amino acid sequence of SEQ ID NO:1. Cells expressing a CAR comprising the modified hinge domain disclosed herein are shown to have enhanced anti-tumor activities with reduced release of pro-inflammatory cytokines.

15 Claims, 17 Drawing Sheets

Specification includes a Sequence Listing.

2nd CAR

2nd-GG CAR

| | 2nd-GG CAR | 2nd CAR |
|---|---|---|
| Top | 18.02 | 25.82 |
| EC50 | 30.40 | 27.52 |

| Conc.(µg/mL) | Relative MFI | |
|---|---|---|
| | 2nd-GG CAR | 2nd CAR |
| 180.00 | 16.59 | 23.92 |
| 72.00 | 13.72 | 22.11 |
| 28.80 | 9.44 | 13.19 |
| 11.52 | 4.67 | 7.08 |
| 4.61 | 2.35 | 3.08 |
| 1.84 | 1.59 | 2.25 |
| 0.74 | 1.30 | 2.05 |
| 0.29 | 1.11 | 1.11 |
| 0.12 | 1.06 | 1.07 |
| 0.05 | 1.06 | 1.03 |

Figure 4F

SEQUENCE LISTING

```
Sequence total quantity: 18
SEQ ID NO: 1              moltype = AA  length = 43
FEATURE                   Location/Qualifiers
REGION                    1..43
                          note = Synthetic Sequence
source                    1..43
                          mol_type = protein
                          organism = synthetic construct
SEQUENCE: 1
TTTPAPRPPT PAPTIASQPL SLRPEACRPA AAVHTRGLDF ACD                    43
```

```
SEQ ID NO: 2        moltype = DNA  length = 129
FEATURE             Location/Qualifiers
misc_feature        1..129
                    note = Synthetic Sequence
source              1..129
                    mol_type = other DNA
                    organism = synthetic construct
SEQUENCE: 2
accactaccc cagcaccgag gccacccacc ccggctccta ccatcgcctc ccagcctctg   60
tccctgcgtc cggaggcatg tagacccgca gctgccgtgc atacccgggg tcttgacttc  120
gcctgcgat                                                          129

SEQ ID NO: 3        moltype = AA  length = 11
FEATURE             Location/Qualifiers
REGION              1..11
                    note = Synthetic Sequence
source              1..11
                    mol_type = protein
                    organism = synthetic construct
SEQUENCE: 3
RASQDISKYL N                                                        11

SEQ ID NO: 4        moltype = AA  length = 7
FEATURE             Location/Qualifiers
REGION              1..7
                    note = Synthetic Sequence
source              1..7
                    mol_type = protein
                    organism = synthetic construct
SEQUENCE: 4
HTSRLHS                                                             7

SEQ ID NO: 5        moltype = AA  length = 9
FEATURE             Location/Qualifiers
REGION              1..9
                    note = Synthetic Sequence
source              1..9
                    mol_type = protein
                    organism = synthetic construct
SEQUENCE: 5
QQGNTLPYT                                                           9

SEQ ID NO: 6        moltype = AA  length = 10
FEATURE             Location/Qualifiers
REGION              1..10
                    note = Synthetic Sequence
source              1..10
                    mol_type = protein
                    organism = synthetic construct
SEQUENCE: 6
GVSLPDYGVS                                                          10

SEQ ID NO: 7        moltype = AA  length = 16
FEATURE             Location/Qualifiers
REGION              1..16
                    note = Synthetic Sequence
source              1..16
                    mol_type = protein
                    organism = synthetic construct
SEQUENCE: 7
VIWGSETTYY NSALKS                                                   16

SEQ ID NO: 8        moltype = AA  length = 12
FEATURE             Location/Qualifiers
REGION              1..12
                    note = Synthetic Sequence
source              1..12
                    mol_type = protein
                    organism = synthetic construct
SEQUENCE: 8
HYYYGGSYAM DY                                                       12

SEQ ID NO: 9        moltype = AA  length = 21
FEATURE             Location/Qualifiers
REGION              1..21
                    note = Synthetic Sequence
source              1..21
                    mol_type = protein
                    organism = synthetic construct
```

```
SEQUENCE: 9
MALPVTALLL PLALLLHAAR P                                                                    21

SEQ ID NO: 10              moltype = DNA   length = 63
FEATURE                    Location/Qualifiers
misc_feature               1..63
                           note = Synthetic Sequence
source                     1..63
                           mol_type = other DNA
                           organism = synthetic construct
SEQUENCE: 10
atggccttac cagtgaccgc cttgctcctg ccgctggcct tgctgctcca cgccgccagg   60
ccg                                                                   63

SEQ ID NO: 11              moltype = AA   length = 242
FEATURE                    Location/Qualifiers
REGION                     1..242
                           note = Synthetic Sequence
source                     1..242
                           mol_type = protein
                           organism = synthetic construct
SEQUENCE: 11
DIQMTQTTSS LSASLGDRVT ISCRASQDIS KYLNWYQQKP DGTVKLLIYH TSRLHSGVPS   60
RFSGSGSGTD YSLTISNLEQ EDIATYFCQQ GNTLPYTFGG GTKLEITGGG GSGGGGSGGG   120
GSEVKLQESG PGLVAPSQSL SVTCTVSGVS LPDYGVSWIR QPPRKGLEWL GVIWGSETTY   180
YNSALKSRLT IIKDNSKSQV FLKMNSLQTD DTAIYYCAKH YYYGGSYAMD YWGQGTSVTV   240
SS                                                                   242

SEQ ID NO: 12              moltype = DNA   length = 441
FEATURE                    Location/Qualifiers
misc_feature               1..441
                           note = Synthetic Sequence
source                     1..441
                           mol_type = other DNA
                           organism = synthetic construct
SEQUENCE: 12
tacacgttcg gaggggggac caagctggag atcacaggtg gcggtggctc gggcggtggt   60
gggtcgggtg gcggcggatc tgaggtgaaa ctgcaggagt caggacctgg cctggtggcg   120
ccctcacaga gcctgtccgt cacatgcact gtctcagggg tctcattacc cgactatggt   180
gtaagctgga ttcgccagcc tccacgaaag ggtctggagt ggctgggagt aatatggggt   240
agtgaaacca catactataa ttcagctctc aaatccagac tgaccatcat caaggacaac   300
tccaagagcc aagtttttctt aaaaatgaac agtctgcaaa ctgatgacac agccatttac   360
tactgtgcca aacattatta ctacggtggt agctatgcta tggactactg gggccaagga   420
acctcagtca ccgtctcctc a                                              441

SEQ ID NO: 13              moltype = AA   length = 24
FEATURE                    Location/Qualifiers
REGION                     1..24
                           note = Synthetic Sequence
source                     1..24
                           mol_type = protein
                           organism = synthetic construct
SEQUENCE: 13
IYIWAPLAGT CGVLLLSLVI TLYC                                            24

SEQ ID NO: 14              moltype = DNA   length = 72
FEATURE                    Location/Qualifiers
misc_feature               1..72
                           note = Synthetic Sequence
source                     1..72
                           mol_type = other DNA
                           organism = synthetic construct
SEQUENCE: 14
atctacattt gggcccctct ggctggtact tgcggggtcc tgctgctttc actcgtgatc   60
actctttact gt                                                         72

SEQ ID NO: 15              moltype = AA   length = 42
FEATURE                    Location/Qualifiers
REGION                     1..42
                           note = Synthetic Sequence
source                     1..42
                           mol_type = protein
                           organism = synthetic construct
SEQUENCE: 15
KRGRKKLLYI FKQPFMRPVQ TTQEEDGCSC RFPEEEEGGC EL                        42

SEQ ID NO: 16              moltype = DNA   length = 126
FEATURE                    Location/Qualifiers
misc_feature               1..126
```

-continued

```
                             note = Synthetic Sequence
source                       1..126
                             mol_type = other DNA
                             organism = synthetic construct
SEQUENCE: 16
aagcgcggtc ggaagaagct gctgtacatc tttaagcaac ccttcatgag gcctgtgcag    60
actactcaag aggaggacgg ctgttcatgc cggttcccag aggaggagga aggcggctgc   120
gaactg                                                              126

SEQ ID NO: 17           moltype = AA  length = 112
FEATURE                 Location/Qualifiers
REGION                  1..112
                        note = Synthetic Sequence
source                  1..112
                        mol_type = protein
                        organism = synthetic construct
SEQUENCE: 17
RVKFSRSADA PAYKQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR           112

SEQ ID NO: 18           moltype = DNA  length = 336
FEATURE                 Location/Qualifiers
misc_feature            1..336
                        note = Synthetic Sequence
source                  1..336
                        mol_type = other DNA
                        organism = synthetic construct
SEQUENCE: 18
cgcgtgaaat tcagccgcag cgcagatgct ccagcctaca agcaggggca gaaccagctc    60
tacaacgaac tcaatcttgg tcggagagag gagtacgacg tgctggacaa gcggagagga   120
cgggacccag aaatgggcgg gaagccgcgc agaaagaatc cccaagaggg cctgtacaac   180
gagctccaaa aggataagat ggcagaagcc tatagcgaga ttggtatgaa aggggaacgc   240
agaagaggca aaggccacga cggactgtac cagggactca gcaccgccac caaggacacc   300
tatgacgctc ttcacatgca ggccctgccg cctcgg                            336
```

CHIMERIC ANTIGEN RECEPTOR WITH MODIFIED HINGE REGION AND USES THEREOF

CROSS REFERENCE TO RELATED APPLICATIONS

This application claims the benefit of U.S. Provisional application No. 63/272,617 filed on Oct. 27, 2021, which is incorporated in their entirety herein by reference.

SEQUENCE LISTING INCORPORATION

The ".xml" Sequence Listing filed with this application by EFS and which is entitled P-608558-US-SQL-15MAY23.xml, is 25 kilobytes in size and which was created on May 15, 2023, is hereby incorporated by reference.

FIELD OF THE INVENTION

The present disclosure is related in general to constructs of chimeric antigen receptor (CAR). In one embodiment, the present disclosure provides improved CAR with modified hinge region.

BACKGROUND OF THE INVENTION

Chimeric antigen receptors (CARs) are recombinant receptors that provide both antigen-binding and T cell activating functions. CART cell therapy, named "Advance of the Year" in 2018 by the American Society of Clinical Oncology, has revolutionized cancer treatment. KYMRIAH® (tisagenlecleucel, Novartis) and YESCARTA® (axicabtagene ciloleucel, Gilead) were rapidly approved by the U.S. Food and Drug Administration, and the number of active clinical trials testing CAR T cells in patients has exploded. Currently, there is substantial interest in improving the efficacy of CAR T cell therapy, e.g. (i) minimizing the toxic side effects of hematologic malignancy-targeted CAR T cells and (ii) improving the efficacy of solid tumor-targeted CAR T cells.

CARs consist of molecules in which tumor antigen recognition and intracellular activation are combined. In general, they minimally contain an extracellular antigen recognition domain linked through a transmembrane domain to an intracellular activation domain or domains. Early CARs consisted of antibody single-chain variable fragments (scFvs) fused through a transmembrane domain to the cytoplasmic tail of the TCR signaling component CD3ζ. Second-generation CARs are those that incorporate a costimulatory domain membrane-proximal to the CD3ζ signaling domain, such as KYMRIAH®, YESCARTA®, and most of the clinically used CARs. Third- and fourth-generation CAR constructs are being developed, with each successive generation adding additional signaling capacity. Third-generation CARs contain two in-line costimulatory domains, whereas fourth-generation CAR T cells typically incorporate separate cytokine signals. Second-generation CARs differ in their choice of costimulatory domain, which affects the efficacy, response phenotype, and metabolic properties of the resulting CAR T cells. The most frequently used costimulatory domains derive from the CD28 family (CD28 and ICOS, Inducible T Cell Costimulator) and the tumor necrosis factor receptor (TNFR) family (4-1BB, CD27, and OX40). KYMRIAH® and YESCARTA® use the same scFv, which recognizes the B cell antigen CD19, but YES- CARTA® incorporates a CD28-derived costimulatory domain, whereas KYMRIAH® incorporates a 4-1BB domain. T cells expressing these two different second-generation CARs have substantial and important functional differences, although the reasons for this are not entirely clear. CD28-based CARs seem to elicit stronger T cell activation as compared with 4-1BB-expressing CARs, tending toward an effector-like phenotype with high interleukin-2 (IL-2) secretion and cytolytic capacity. However, in vivo persistence of CD28-based CARs is limited, and they are more prone to activation-induced cell death. In contrast, 4-1BB-based CART cells tend toward a central memory phenotype with slower effector response. 4-1BB CAR T cells are also more persistent, due to decreased exhaustion and up-regulation of BCL-2 family members, and have been found in vivo even years after treatment. It is likely that these strikingly distinct phenotypes arise from their activation of different downstream pathways.

CAR T cell therapy has transformed the care of refractory B cell malignancies and holds tremendous promise for many aggressive tumors. Despite remarkable efficacy in the treatment of some malignancies, CAR T cell therapy has several notable adverse reactions which can be life threatening. The most common severe reaction to CAR T cell therapy is the cytokine release syndrome (CRS). CRS occurs after the hundreds of millions of infused T cells release cytokines in a positive feedback loop, causing a systematic inflammatory response syndrome (SIRS). The SIRS reaction present in CRS can be clinically indistinguishable from sepsis and septic shock, with fevers, tachycardia, hypotension, and multiple organ system dysfunctions. Therefore, it is very important to reduce the frequency as well as the severity of CRS caused by CAR T cell therapy.

At the same time, some patients do not respond to anti-CD19 CAR T cell therapy. The reasons may be related to the patient's large tumor burden, the patient's T lymphocyte dysfunction, and the patient's complex immunosuppressive microenvironment.

One of the important topics in CAR T cell research is whether the effectiveness of CAR T cell therapy can be improved by optimizing the structure of CAR. At present, optimization of CAR structural elements mainly focuses on the signaling elements of CAR, namely, the antigen recognition site and the costimulatory signaling domain. For example, the affinity of the antigen recognition region (e.g. scFv) for the target protein may be adjusted so that it can only recognize target antigen expressed on tumor cells, but not those expressed on normal cells so as to avoid on target off tumor effect. There are also results indicating CARs with different costimulatory domains would confer different biological effects. Compared to cells expressing CARs that contain the CD28 costimulatory domain, cells expressing CARs with the 4-1BB costimulatory domain tend to have slower effector response and longer persistent in the host. Researchers have also tried to optimize the three immunoreceptor tyrosine activation motifs (ITAMs) of CD3ζ, and it was found that CAR T cells with one mutated ITAM have stronger anti-tumor activity due to avoidance of cell death caused by over-activation. However, currently there is very little research on whether the effectiveness of CAR T cell therapy can be improved by optimizing the non-signaling domains of CAR.

Thus, there is a need for optimizing the structure of CAR to enhance the effectiveness of CAR T cell therapy.

SUMMARY OF THE INVENTION

In one embodiment, the present disclosure provides an isolated chimeric antigen receptor (CAR) molecule comprising an antigen binding domain, a hinge domain, a transmembrane domain, a costimulatory domain, and an intracellular signaling domain, wherein the hinge domain comprising the amino acid sequence of SEQ ID NO:1. In one embodiment, the hinge domain is encoded by a nucleotide sequence comprising the sequence of SEQ ID NO:2.

In one embodiment, the antigen binding domain of the CAR disclosed herein is a single chain antibody or single chain antibody fragment. In one embodiment, the antigen binding domain binds to a target antigen such as CD19. Other examples of target antigen include, but are not limited to, CD20, CD22, CD33, CD123, BCMA, CLL1, CD7, CS1, CEA, AFP, PSMA, GPC3, GD2, EGFRVIII, NKG2D, Mesothelin, Claudin 18.2, ROR3, and Muc1. One of ordinary skill in the art would readily incorporate into the CAR disclosed herein an antigen binding domain that would bind to any other target antigen of interest.

In one embodiment, the antigen binding domain of the CAR disclosed herein binds to CD19 and comprises a light chain complementary determining region 1 (LC CDR1) having the amino acid sequence of SEQ ID NO:3, a light chain complementary determining region 2 (LC CDR2) having the amino acid sequence of SEQ ID NO:4, a light chain complementary determining region 3 (LC CDR3) having the amino acid sequence of SEQ ID NO:5, and a heavy chain complementary determining region 1 (HC CDR1) having the amino acid sequence of SEQ ID NO:6, a heavy chain complementary determining region 2 (HC CDR2) having the amino acid sequence of SEQ ID NO:7, and a heavy chain complementary determining region 3 (HC CDR3) having the amino acid sequence of SEQ ID NO:8.

In one embodiment, the antigen binding domain of the CAR disclosed herein comprises a scFv that binds to CD19, and the scFv comprises the amino acid sequence of SEQ ID NO:11.

In one embodiment, the transmembrane domain of the CAR disclosed herein comprises a transmembrane domain of one of the following proteins: the alpha, beta or zeta chain of T cell receptor, CD28, CD3 epsilon, CD45, CD4, CD5, CD8, CD9, CD16, CD22, CD33, CD37, CD64, CD80, CD86, CD134, CD137 and CD154.

In one embodiment, the costimulatory domain of the CAR disclosed herein comprises a functional signaling domain of one of the following proteins: OX40, CD2, CD27, CD28, CDS, ICAM-1, LFA-1 (CD11a/CD18), ICOS (CD278), and 4-1BB (CD137).

In one embodiment, the intracellular signaling domain of the CAR disclosed herein comprises an intracellular signaling domain of CD3 zeta, or FcR gamma, or a functional fragment thereof. One of ordinary skill in the art would readily recognize that the intracellular signaling domain of the CAR disclosed herein may comprise any other suitable signaling domain known in the art.

In one embodiment, the present disclosure provides a nucleic acid construct comprising one or more nucleic acid sequences that encode the CAR disclosed herein, or fragments thereof. In another embodiment, there is provided an expression vector comprising the above nucleic acid construct. In another embodiment, there is provided a cell comprising the above expression vector. In another embodiment, there is provided a cell comprising the CAR disclosed herein. In another embodiment, there is provided a composition comprising the cell described above and a pharmaceutically acceptable carrier. In one embodiment, the cell is an immune cell. In one embodiment, the immune cell is a T cell.

In one embodiment, the present disclosure also provides a method of using the cells (e.g. T cells) expressing the CAR disclosed herein to treat cancer.

These and other aspects of the invention will be appreciated from the ensuing descriptions of the figures and detailed description of the invention.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIG. 1A: Diagrammatic model of 2nd and 2nd-GG CAR. Schematic of CAR containing scfv (FMC63), variations in the hinge, extra-membrane, and transmembrane domains. The hinge region of 2nd-GG deleted two Gly compared with that of the 2nd CAR, and the rest of the sequences were the same. FIG. 1B: Typical flow cytometry detection of the expression efficiency of 2nd and 2nd-GG CAR on T cells. FIG. 1C: Expression efficiency of 2nd and 2nd-GG on T cells 5-6 days after culture in vitro determined by flow cytometry (mean±SD, n=5). T cells are derived from at least three different healthy donors. FIG. 1D: Comparison of the flexibility between the CD8 hinge and the CD8-GG hinge. S2 order parameter (S2 RCI) values were estimated from chemical shift values using the Random Coil Index (RCI) software. S2 is inversely proportional to the hinge region flexibility. FIG. 1E: The affinity of CD19 protein to different CAR T cells: 2nd CAR-T cells>2nd-GG CAR-T cells. The EC50 of 2nd and 2nd-GG CAR-T cells binding to CD19 protein was determined by flow cytometry. EC50, 50% maximal effective concentration. CAR, chimeric antigen receptor; FITC, fluorescein isothiocyanate.

FIG. 2A: Cytotoxic percentages of targeted cells by mock T, 2nd and 2nd-GG CAR-T cells after 8-10 h of co-culture in vitro. E:T (2.5:1 and 5:1) designate the ratios of the absolute number of CART cells to target cells, specifically K562, NALM-6, 786o-CD19, and K562-CD19. The number of mock T cells is the same as in the 2nd CAR-T cells group. Results are representative of at least three independent experiments with T cells from different healthy donors. FIG. 2B: Human IFNγ, TNF-a, IL-2 and IL-6 production by mock T, 2nd and 2nd-GG CAR-T cells. Cytokine concentrations in the media were measured after 24 h of co-incubation with different target cells at E:T of 1:1. Values are mean±SD of triplicate specimens obtained with T cells isolated from one healthy donor. *P<0.05; P<0.01; *P<0.005.

FIG. 3A: Diagrammatic representations of the experimental procedures. FIG. 3B: Representative bioluminescent images are shown. FIG. 3C: Overall survival curves of NALM-6-GFP-luc challenged mice (n=8). FIG. 3D: Tumor burden-total flux (log) for each mouse was quantified and averaged by group. (mean±SEM). FIG. 3E: On day 8, approximately 1,000 μL of blood were collected from the caudal vein of each mouse mixed to detect the concentration of human IL-2, TNF-α, IFN-γ, and IL-6 using an ELISA-kit. (mean±SD, n=2). ***P<0.005.

FIGS. 4A-4F show antitumor efficacy and cytokines release of different CAR-T cells in high tumor load models. FIG. 4A: Diagrammatic representations of the experimental procedures. FIG. 4B: Representative bioluminescent images are shown. FIG. 4C: Overall survival curves of NALM-6-GFP-luc challenged mice (n=8). FIG. 4D: Tumor burden-total flux (log) for each mouse was quantified and averaged by group. (mean±SEM). FIG. 4E: On day 14, one mouse was randomly euthanized from the Mock-T, 2nd CAR-T and 2nd-GG CAR-T groups. Cell suspensions from peripheral blood, bone marrow and spleen were collected and ground for flow cytometry detection. Since the NALM-6 cells were engineered to express GFP, the tumor load was reflected by the expression percentage of GFP+ cells. FIG. 4F: On day 12, approximately 1,000 µL of blood were collected from the caudal vein of each mouse to detect the concentration of human IL-2, TNF-α, IFN-γ, and IL-6 using an ELISA-kit. (mean±SD, n=2). P<0.01, *P<0.005.

DETAILED DESCRIPTION OF THE INVENTION

Figure 1A:
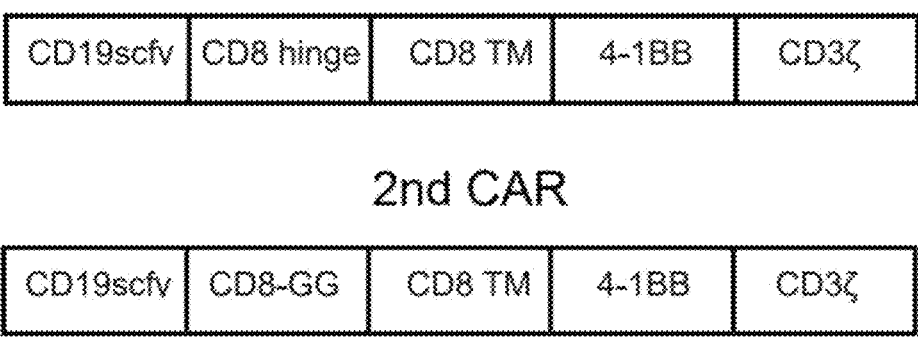
FIGS. 1A-1E present schematic diagram and expression efficiency of 2nd and 2nd-GG CAR-T cells.

The present specification discloses a new structure for chimeric antigen receptor (CAR). The design of the new CAR is based on optimizing the CD8 hinge region in the classic second-generation CAR structure. The new CAR comprises a CD8 hinge region where two amino acids (Gly-Gly) are removed in order to reduce its flexibility. The new CAR disclosed herein is designated as 2nd-GG CAR, whereas the classic second-generation CAR is designated as 2nd CAR. Through in vivo and in vitro experiments, it was found that T cells expressing the new 2nd-GG CAR control CD19+ tumors more effectively than T cells expressing the classic second-generation CAR. Moreover, as compared to T cells expressing the classic second-generation CAR, T cells expressing the new 2nd-GG CAR induce less release of pro-inflammatory cytokines.

In one embodiment, the CAR disclosed herein comprises an antigen binding domain, a hinge domain, a transmembrane domain, a costimulatory domain, and an intracellular signaling domain, wherein the hinge domain comprising the amino acid sequence of SEQ ID NO:1. One of ordinary skill in the art would readily select and construct an antigen binding domain, a transmembrane domain, a costimulatory domain, and an intracellular signaling domain to be incorporated in the CAR disclosed herein. These various domains will be further discussed below.

In one embodiment, the present invention provides a new type of CAR that can specifically kill tumor cells expressing CD19. T cells expressing the new 2nd-GG CAR can more effectively control tumor burden in murine models, and cause less secretion of pro-inflammatory cytokines. In one embodiment, the new CAR comprises an anti-CD19 scFv, a modified CD8 hinge domain (CD8-GG), a CD8 transmembrane domain, a 4-1BB costimulatory domain, and a CD3 zeta signaling domain.

The present invention relates to novel polypeptides comprising the improved CAR disclosed herein and polynucleotides encoding the same. The present invention also provides vectors (e.g., viral vectors) comprising such polynucleotides and compositions comprising such vectors. The present invention also provides polynucleotides encoding the CAR disclosed herein and compositions comprising such polynucleotides. The present invention additionally provides engineered cells (e.g., T cells) comprising such polynucleotides and/or transduced with such vectors and compositions comprising such engineered cells. In one embodiment, the present invention provides compositions (e.g., pharmaceutical compositions) including a plurality of such engineered T cells. The present invention also provides methods for manufacturing such engineered T cells and compositions and uses (e.g., in treating a B cell lymphoma) of such engineered T cells and compositions. In another embodiment, the present invention provides a method of inducing immunity against a tumor comprising administering to a subject an effective amount of a cell comprising a polynucleotide, a vector, or a polypeptide of the present invention. In another embodiment, the present invention relate to cells comprising the CAR and their use in a T cell therapy, e.g., an autologous cell therapy for the treatment of a patient suffering from a cancer.

As used herein, the terms "comprise", "comprises", "comprising", "includes", "including", "having" and their conjugates mean "including but not limited to".

As used herein, the singular form "a", "an" and "the" include plural references unless the context clearly dictates otherwise.

Throughout this application, various embodiments of the present disclosure may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting. Each literature reference or other citation referred to herein is incorporated herein by reference in its entirety.

As used herein, an "antigen binding molecule," "antigen binding domain," or "antibody fragment" refers to any molecule that comprises the antigen binding parts (e.g., CDRs) of the antibody from which the molecule is derived. An antigen binding molecule can include the antigenic complementarity determining regions (CDRs) that can be readily determined by one of ordinary skill in the art. Examples of antibody fragments include, but are not limited to, Fab, Fab', F(ab')2, Fv fragments, dAb, linear antibodies, scFv, and multispecific antibodies formed from antigen binding molecules. Peptibodies (i.e., Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyper-proliferative disease or to a viral or bacterial antigen. In certain embodiments, the antigen binding molecule binds to CD19. In further embodiments, the antigen binding molecule is an antibody fragment that specifically binds to the antigen, including one or more of the complementarity determining regions (CDRs) thereof.

In some embodiments, the antigen binding molecule is a single chain variable fragment (scFv) as it is generally known in the art. A scFv polypeptide molecule is a covalently linked $V_H$-$V_L$ heterodimer, which can be expressed from a gene fusion including $V_H$- and $V_L$-encoding genes linked by linker. The linker peptide (e.g., of about ten to about 25 amino acids) is usually rich in glycine for flexibility, as well as serine or threonine for solubility. The linker may either connect the N-terminus of the VH with the C-terminus of the VL or connect the C-terminus of the VH with the N-terminus of the VL. This protein retains the specificity of the original immunoglobulin, despite removal of the constant regions and the introduction of the linker. An scFv may also include an N-terminal peptide sequence, which sometimes is referred to as a "signal peptide" or "leader sequence". A number of methods are available to one of ordinary skill in the art to construct a scFv from the light and heavy chain variable regions of an antibody, see e.g., U.S. Pat. Nos. 5,091,513; 5,132,405; and 4,946,778.

The terms "VL", "VL region", and "VL domain" are used interchangeably to refer to the light chain variable region of an antigen binding domain such as an antibody or an antigen-binding fragment thereof, and comprise one, two, or all three CDRs.

The terms "VH", "VH region", and "VH domain" are used interchangeably to refer to the heavy chain variable region of an antigen binding domain such as an antibody or an antigen-binding fragment thereof, and comprise one, two, or all three CDRs.

As it is generally known in the art, there are a number of commonly used definitions of CDRs, such as Kabat numbering, Chothia numbering, AbM numbering, or contact numbering.

As used herein, the terms "genetic engineering" or "engineering" are used interchangeably and mean a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which may either be obtained from a patient or a donor. The cell may be modified to express an exogenous construct, such as the CAR disclosed herein, which is incorporated into the cell's genome.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor. Examples of cancers that can be treated by the methods of using the CAR disclosed herein include, but are not limited to, cancers of the immune system including lymphoma, leukemia, myeloma, and other leukocyte malignancies.

In some embodiments, cancers that can be treated by the methods of using the CAR disclosed herein include, but are not limited to, B-cell lymphomas, acute lymphoblastic leukemia (ALL), AIDS-related lymphoma, ALK-positive large B-cell lymphoma, Burkitt's lymphoma, chronic lymphocytic leukemia, (CLL), classical Hodgkin lymphoma, diffuse large B-cell lymphoma (DLBCL), follicular lymphoma, intravascular large B-cell lymphoma, large B-cell lymphoma arising in HHV8-associated multicentric Castleman's disease, lymphomatoid granulomatosis, lymphoplasmacytic lymphoma, mantle cell lymphoma (MCL), marginal zone B-cell lymphoma (MZL), mucosa-associated lymphatic tissue lymphoma (MALT), nodal marginal zone B cell lymphoma (NMZL), nodular lymphocyte predominant Hodgkin's lymphoma, non-Hodgkin's lymphoma, plasmablastic lymphoma, primary central nervous system lymphoma, primary effusion lymphoma, splenic marginal zone lymphoma (SMZL), and Waldenstrom's macroglobulinemia, or a combination thereof.

An "anti-tumor effect" as used herein refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine.

A "therapeutically effective amount," "effective dose," "effective amount," or "therapeutically effective dosage" of a therapeutic agent, e.g., engineered T cells expressing the CAR disclosed herein, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In one embodiment, "treatment" or "treating" includes a partial remission. In another embodiment, "treatment" or "treating" includes a complete remission.

Chimeric Antigen Receptors (CAR)

As it is generally known in the art, chimeric antigen receptors are genetically engineered receptors comprising at least an extracellular antigen binding domain, a hinge domain, a transmembrane domain and a cytoplasmic signaling domain. These engineered receptors can be readily inserted into and expressed by immune cells, such as T cells in accordance with techniques known in the art. With a CAR, a single receptor can be programmed to both recognize a specific antigen and, when bound to that antigen, activates the immune cell to attack and destroy the cell bearing that antigen. When these antigens exist on tumor cells, an immune cell that expresses the CAR can target and kill the tumor cell.

In some embodiments, the present invention relates to CARs comprising a modified hinge domain having the amino acid sequence of SEQ ID NO: 1. In some embodiments, the present invention relates to CARs comprising the modified hinge domain disclosed herein and an antigen binding domain, such as a scFv, that specifically binds to a tumor-associated antigen, e.g. human CD19. In other embodiments, the present invention also relates to engineered T cells expressing such CARs.

As used herein, the term "tumor associated antigen" (TAA) encompasses a molecule or a portion thereof, which is displayed on the surface of a cell or a molecule which is present within the milieu of a tumor, that is within the tumor micro-environment (TME). In some embodiments, a TAA encompasses a cell surface tumor associated antigen (TAA). In some embodiments, the cell is a tumor cell. In some embodiments, the cell is a non-tumor cell present in the milieu of a tumor, for example but not limited to a cell present within vasculature tissue associated with a tumor or cancer. In some embodiments, a TAA is an angiogenic antigen in a tumor micro-environment. In some embodiments, a TAA is an antigen on a blood vessel in a tumor micro-environment. In some embodiments, the cell is a stromal cells present in the milieu of a tumor. In some embodiments, a TAA is a stromal cell antigen within a tumor micro-environment. In some embodiments, a TAA encompasses an extracellular epitope of a tumor-cell-surface antigen. In some embodiments, a TAA encompasses an extracellular matrix antigen.

In some embodiments, a TAA comprises an antigen present in a TME. In some embodiments, a TAA comprises a molecule secreted by a tumor cell into the TME. In some embodiments, a TAA comprises an effector molecule secreted by a tumor cell into the TME. In some embodiments, a TAA comprises an effector molecule secreted by a tumor cell into the TME in order to downregulate or inhibit the activity of cytotoxic natural killer (NK) or T cells. In some embodiments, a TAA comprises soluble activating receptor ligand secreted by a tumor cell into the TME in order to block the recognition of the tumor cell by a NK cell or T cell. In some embodiments, a TAA comprises a suppressive immune cell in the TME that would otherwise inhibit NK cell activation.

In some embodiments, the tumor associated antigen (TAA) is a tumor antigen. In some embodiments, tumor antigens comprise those antigens are presented on tumor cells. In some embodiments, the tumor antigen is present on a cell of solid tumor. In some embodiments, the tumor antigen is a cancer antigen, present on a cell of a non-solid tumor.

In some embodiments, the solid tumor comprises a sarcoma or a carcinoma, a fibrosarcoma, a myxosarcoma, a liposarcoma, a chondrosarcoma, an osteogenic sarcoma, a chordoma, an angiosarcoma, an endotheliosarcoma, a lymphangiosarcoma, a lymphangioendotheliosarcoma, a synovioma, a mesothelioma, an Ewing's tumor, a leiomyosarcoma, a rhabdomyosarcoma, a colon carcinoma, a pancreatic cancer or tumor, a breast cancer or tumor, an ovarian cancer or tumor, a prostate cancer or tumor, a squamous cell carcinoma, a basal cell carcinoma, an adenocarcinoma, a sweat gland carcinoma, a sebaceous gland carcinoma, a papillary carcinoma, a papillary adenocarcinomas, a cystadenocarcinoma, a medullary carcinoma, a bronchogenic carcinoma, a renal cell carcinoma, a hepatoma, a bile duct carcinoma, a choriocarcinoma, a seminoma, an embryonal carcinoma, a Wilm's tumor, a cervical cancer or tumor, a uterine cancer or tumor, a testicular cancer or tumor, a lung carcinoma, a small cell lung carcinoma, a bladder carcinoma, an epithelial carcinoma, a glioma, an astrocytoma, a medulloblastoma, a craniopharyngioma, an ependymoma, a pinealoma, a hemangioblastoma, an acoustic neuroma, an oligodenroglioma, a schwannoma, a meningioma, a melanoma, a neuroblastoma, or a retinoblastoma. In some embodiments, the solid tumor comprises an adrenocortical tumor (adenoma and carcinoma), a colorectal carcinoma, a desmoid tumor, a desmoplastic small round cell tumor, an endocrine tumor, an Ewing sarcoma, a germ cell tumor, a hepatoblastoma a hepatocellular carcinoma, an osteosarcoma, a soft tissue sarcoma other than rhabdomyosarcoma, and a Wilms tumor.

In one embodiment, the TAA can be, but is not limited to, CD19, 5T4, ROR1, EGFR, FcγRI, FcγRIIa FcγRIIb FcγRIIIa FcγRIIIb, CD28, CD137, CTLA-4, FAS, FAP (Fibroblast activation protein), LGR5, C5aR1, A2AR, fibroblast growth factor receptor 1 (FGFR1), FGFR2, FGFR3, FGFR4, glucocorticoid-induced TNFR-related (GITR) protein, lymphotoxin-beta receptor (LTβR), toll-like receptors (TLR), tumor necrosis factor-related apoptosis-inducing ligand-receptor 1 (TRAIL receptor 1), TRAIL receptor 2, prostate-specific membrane antigen (PSMA) protein, prostate stem cell antigen (PSCA) protein, tumor-associated protein carbonic anhydrase IX (CAIX), epidermal growth factor receptor 1 (EGFR1), EGFRvIII, human epidermal growth factor receptor 2 (Her2/neu; Erb2), ErbB3 (HER3), Folate receptor, ephrin receptors, PDGFRa, ErbB-2, CD20, CD22, CD30, CD33, CD40, CD37, CD38, CD70, CD74, CD56, CD40), CD80, CD86, CD2, p53, cMet (tyrosine-protein kinase Met) (hepatocyte growth factor receptor) (HGFR), MAGE-A1, MAGE-A2, MAGE-A3, MAGE-A4, MAGE-A6, MAGE-A10, MAGE-A12, BAGE, DAM-6, DAM-10, GAGE-1, GAGE-2, GAGE-8, GAGE-3, GAGE-4, GAGE-5, GAGE-6, GAGE-7B, NA88-A, NY-ESO-1, BRCA1, BRCA2, MART-1, MC1R, Gp100, PSA, PSM, Tyrosinase, Wilms' tumor antigen (WT1), TRP-1, TRP-2, ART-4, CAMEL, Cyp-B, hTERT, hTRT, iCE, MUC1, MUC2, P-cadherin, Myostatin (GDF8), Cripto (TDGF1), MUC5AC, PRAME, P15, RU1, RU2, SART-1, SART-3, WT1, AFP, f3-catenin/m, Caspase-8/m, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mbcr-abl, ETV6/AML, LDLR/FUT, Pml/RARα, TEL/AML1, CD28, CD137, CanAg, Mesothelin, DRS, PD-1, PD1L, IGF-1R, CXCR4, Neuropilin 1, Glypicans, EphA2, CD138, B7-H3, B7-H4, gpA33, GPC3, SSTR2, or VEGF-R2.

In one embodiment, the antigen binding domain of the CAR disclosed herein binds to CD19. In one embodiment, the anti-CD19 antigen binding domain comprises a light chain complementary determining region 1 (LC CDR1) having the amino acid sequence of SEQ ID NO:3, a light chain complementary determining region 2 (LC CDR2) having the amino acid sequence of SEQ ID NO:4, a light chain complementary determining region 3 (LC CDR3) having the amino acid sequence of SEQ ID NO:5, and a heavy chain complementary determining region 1 (HC CDR1) having the amino acid sequence of SEQ ID NO:6, a heavy chain complementary determining region 2 (HC CDR2) having the amino acid sequence of SEQ ID NO:7, and a heavy chain complementary determining region 3 (HC CDR3) having the amino acid sequence of SEQ ID NO:8.

In one embodiment, the anti-CD19 antigen binding domain comprises a scFv, and the scFv comprises the amino acid sequence of SEQ ID NO:11.

Transmembrane Domains

The transmembrane domain is designed to be fused to the extracellular domain of the CAR, as well as being fused to the intracellular domain of the CAR. In some embodiments, the transmembrane domain can be selected or modified by amino acid substitution to avoid binding of such domains to the transmembrane domains of the same or different surface membrane proteins to minimize interactions with other members of the receptor complex. The transmembrane domain can be derived either from a natural or from a synthetic source. Where the source is natural, the domain can be derived from any membrane-bound or transmembrane protein. In some embodiments, transmembrane domains that can be incorporated into the CAR disclosed herein include, but are not limited to, the transmembrane domains of one of the following proteins: 4-1BB/CD137, activating NK cell receptors, an immunoglobulin protein, B7-H3, BA1-41-4R, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, a ligand that specifically binds with CD83, LIGHT, LIGHT, LTBR, Ly9 (CD229), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), signaling lymphocytic activation molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, TNFSF14, a Toll ligand receptor, TRANCE/RANKL, VLA1, or VLA-6, or a fragment, truncation, or a combination thereof. One of ordinary skill in the art would readily recognize and determine a transmembrane domain from these proteins. The polypeptide sequences of these transmembrane domains, as well as the polynucleotide sequences encoding the same, are well-known in the art.

In some embodiments, the polypeptide sequence of a transmembrane domain comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the polypeptide sequence of which is known in the art. In some embodiments, the polynucleotide encoding a transmembrane domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of which is known in the art. Optionally, short linkers can be used to form linkages between any or some of the extracellular, transmembrane, and intracellular domains of the CAR.

Costimulatory Domains

As it is known in the art, the costimulatory domain of a CAR is designed to provide costimulatory signaling to an activating domain, which then activates at least one of the normal effector functions of the immune cell. Effector function of a T cell, for example, can be cytolytic activity or helper activity including the secretion of cytokines.

In certain embodiments, suitable costimulatory domains include (i.e., comprise), but are not limited to, the costimulatory domain of 4-1BB/CD137, activating NK cell receptors, an immunoglobulin protein, B7-H3, BA1-41-4R, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, ligand that specifically binds with CD83, LIGHT, LIGHT, LTBR, Ly9 (CD229), Ly108), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof. One of ordinary skill in the art would readily recognize and determine a costimulatory domain from these proteins. The polypeptide sequences of these costimulatory domains, as well as the polynucleotide sequences encoding the same, are well-known in the art.

In some embodiments, the polypeptide sequence of a costimulatory domain comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the polypeptide sequence of which is known in the art. In some embodiments, the polynucleotide encoding a costimulatory domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of which is known in the art.

Intracellular Signaling/Activating Domains

Intracellular signaling or activating domains that can be incorporated into a CAR is generally known in the art. For example, CD3 is an element of the T cell receptor on native T cells, and has been shown to be an important intracellular activating element in CARs. In some embodiments, the CD3 is CD3-zeta or CD3-epsilon, the polynucleotide and polypeptide sequences of each of which are well-known in the art.

In some embodiments, the polypeptide sequence of an intracellular signaling or activating domain comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the polypeptide sequence of which is known in the art. In some embodiments, the polynucleotide encoding an intracellular signaling or activating domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of which is known in the art.

Leader Peptides or Leader Sequences

In some embodiments, the CAR of the present invention may further comprise a leader peptide (also referred to herein as a "signal peptide" or "leader sequence"). Leader peptides suitable for incorporation in CAR are well-known in the art. In certain embodiments, the leader peptide comprises an amino acid sequence that is at least about 75%, at least about 80%, at least about 85%, at least about 90%, at least about 95%, at least about 96%, at least about 97%, at least about 98%, at least about 99%, or 100% identical to the amino acid sequence of leader sequences known in the art.

Vectors, Cells, and Pharmaceutical Compositions

In another embodiment, provided herein are nucleic acid constructs comprising one or more nucleic acid sequences that encode the CAR disclosed herein, or fragments thereof. In another embodiment, provided herein are expression vectors comprising the above nucleic acid constructs.

Any vector known in the art is suitable for the present invention. In some embodiments, the vector is a viral vector. In some embodiments, the vector can be, but is not limited to, a retroviral vector, a DNA vector, a murine leukemia virus vector, an SFG vector, a plasmid, a RNA vector, an adenoviral vector, a baculoviral vector, an Epstein Barr viral vector, a papovaviral vector, a vaccinia viral vector, a herpes simplex viral vector, an adenovirus associated vector (AAV), a lentiviral vector, or any combination thereof.

In other aspects, provided herein are cells comprising the nucleic acid constructs or vectors described above. In some embodiments, the present invention is directed to cells comprising a polynucleotide encoding the CAR as described herein. In other embodiments, the present invention is directed to cells comprising the CAR as described herein.

Any cell may be used as a host cell for the polynucleotides, the vectors, or the polypeptides of the present invention. In some embodiments, the cell can be a prokaryotic cell, fungal cell, yeast cell, or higher eukaryotic cells such as a mammalian cell. Suitable prokaryotic cells generally known in the art include, without limitation, eubacteria, such as Gram-negative or Gram-positive bacteria. In some embodiments, the cell is a human cell. In some embodiments, the cell is an immune cell. In some embodiments, the immune cell can be a T cell, a B cell, a tumor infiltrating lymphocyte (TIL), a TCR expressing cell, a natural killer (NK) cell, a dendritic cell, a granulocyte, an innate lymphoid cell, a megakaryocyte, a monocyte, a macrophage, a platelet, a thymocyte, or a myeloid cell. In one embodiment, the immune cell is an allogeneic T cell, a heterologous T cell, or any combination thereof.

The cell of the present invention may be obtained through any source known in the art. For example, T cells can be differentiated in vitro from a hematopoietic stem cell population, or T cells can be obtained from a subject. T cells can be obtained from, e.g., peripheral blood mononuclear cells, bone marrow, lymph node tissue, cord blood, thymus tissue, tissue from a site of infection, ascites, pleural effusion, spleen tissue, or tumors. In addition, the T cells can be derived from one or more T cell lines available in the art. Methods for isolating T cells for T cell therapy are generally known in the art, e.g. in U.S. Patent Publication No. 2013/0287748, which is herein incorporated by references in its entirety.

Pharmaceutical compositions of the present invention may comprise a cell expressing the CAR disclosed herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration are determined by such factors as the condition of the patient, and the type and severity of the patient's disease according to practices generally known in the art.

Uses of the CAR

Another aspect of the invention is directed to a method of making a cell expressing the CAR disclosed herein. In some embodiments, the method comprises transducing a cell with a polynucleotide encoding the CAR disclosed herein. In some embodiments, the method comprises transducing a cell with a vector comprising polynucleotide sequences encoding the CAR disclosed herein.

Another aspect of the present invention is directed to a method of inducing immune responses against a tumor comprising administering to a subject an effective amount of cells comprising the polynucleotide described herein, the vector described herein, or the CAR described herein. In one embodiment, the method comprises administering to a subject an effective amount of cells comprising a polynucleotide encoding the CAR disclosed herein. In another embodiment, the method comprises administering to a subject an effective amount of cells comprising a vector comprising polynucleotide sequences encoding the CAR disclosed herein. In another embodiment, the method comprises administering to a subject an effective amount of cells comprising the CAR disclosed herein. An "immune response" refers to the action of a cell of the immune system (for example, T lymphocytes, B lymphocytes, natural killer (NK) cells, macrophages, eosinophils, mast cells, dendritic cells or neutrophils) and soluble macromolecules produced by any of these cells (for example antibodies, cytokines, and complement) that results in selective targeting, binding to, damage to, destruction of, and/or elimination from a vertebrate's body of invading pathogens, cells or tissues infected with pathogens, cancerous or other abnormal cells.

Another aspect of the present invention is directed to a method of using the CAR disclosed herein to treat a cancer in a subject in need thereof. In one embodiment, the method comprises administering to the subject polynucleotide sequences encoding the CAR disclosed herein. In another embodiment, the method comprises administering a vector comprising polynucleotide sequences encoding the CAR disclosed herein. In another embodiment, the method comprises administering to the subject cells (e.g. T cells) expressing the CAR disclosed herein. T cells can be isolated from the subject (or from a third party) and be engineered to express the CAR disclosed herein according to commonly used techniques in the art.

In some embodiments, T cells engineered to express the CAR disclosed herein can be administered to a subject or patient at a therapeutically effective amount. For example, a therapeutically effective amount of the T cells can be at least about $10^4$ cells, at least about $10^5$ cells, at least about $10^6$ cells, at least about $10^7$ cells, at least about $10^8$ cells, at least about $10^9$, or at least about $10^{10}$. In some embodiments, the therapeutically effective amount of the engineered CAR T cells is about $2 \times 10^6$ cells/kg, about $3 \times 10^6$ cells/kg, about $4 \times 10^6$ cells/kg, about $5 \times 10^6$ cells/kg, about $6 \times 10^6$ cells/kg, about $7 \times 10^6$ cells/kg, about $8 \times 10^6$ cells/kg, about $9 \times 10^6$ cells/kg, about $1 \times 10^7$ cells/kg, about $2 \times 10^7$ cells/kg, about $3 \times 10^7$ cells/kg, about $4 \times 10^7$ cells/kg, about $5 \times 10^7$ cells/kg, about $6 \times 10^7$ cells/kg, about $7 \times 10^7$ cells/kg, about $8 \times 10^7$ cells/kg, or about $9 \times 10^7$ cells/kg.

The methods described above can be used to treat a cancer in a subject, reduce the size of a tumor, kill tumor cells, prevent tumor cell proliferation, prevent growth of a tumor, eliminate a tumor from a patient, prevent relapse of a tumor, prevent tumor metastasis, induce remission in a patient, or any combination thereof. In certain embodiments, the methods induce a complete response. In other embodiments, the methods induce a partial response.

In some embodiments, the methods described above may further comprise administering a second therapeutic. Examples for the second therapeutic include, but are not limited to, a chemotherapeutic agent, a radioactive therapeutic agent, a cytokine, or a cytokine inhibitor. In some embodiments, compositions comprising cells expressing the CAR disclosed herein, and the second therapeutic are administered each in an amount effective to treat the disease or condition in the subject. In certain embodiments, compositions comprising cells expressing the CAR disclosed herein may be administered prior to, in conjunction with, and/or subsequent to the administration of the second therapeutic.

In the description presented herein, each of the steps of the invention and variations thereof are described. This description is not intended to be limiting and changes in the components, sequence of steps, and other variations would be understood to be within the scope of the present invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Example 1

Reducing Hinge Flexibility of CAR-T Cells Prolongs Survival In Vivo with Low Cytokines Release Materials and Methods Cell Lines and Cell Culture Conditions Cell lines were cultured according to the manufacturers' recommendations. NALM-6 is a pre-B cell acute lymphoblastic leukemia (ALL) cell line with high expression of CD19 (German DSMZ cell collection Cat #: ACC128). NALM-6-GFP-luciferase (luc) is a stable cell line engineered to express GFP-luciferase. K562 is a chronic myelogenous leukemia cell line (ATCC; Cat #: CCL-243). K562-CD19 and K562-CD19-GFP are stable cell lines engineered to express CD19 and/or GFP. 786o is a renal cell adenocarcinoma cell line (ATCC; Cat #: CRL-1932™). CD19 was transduced using a lentivirus system into 786o to produce 786o-CD19. The method of tumor cells culture is described in Zhang et al. Secretion of Human Soluble Programmed Cell Death Protein 1 by Chimeric Antigen Receptor-Modified T Cells Enhances Anti-Tumor Efficacy. Cytotherapy (2020) 22 (12):734-43.

Generation of CAR Constructs

Generation of lentiviral constructs and production of lentiviral particles are described in Kutner et al. Production, Concentration and Titration of Pseudotyped HIV-1-Based Lentiviral Vectors. Nat Protoc (2009) 4(4):495-505. The conventional second-generation 2nd CAR was constructed by the fusion of CD19 scFv, CD8 hinge and transmembrane, 4-1BB, and CD3z. The structure of 2nd-GG is same to the 2nd CAR except for deletion of two consecutive glycine in the CD8 hinge.

Selection, Activation, and Lentivector Transduction of CD3+ T Cells

Blood samples from healthy volunteers were obtained using an approved protocol by the Ethics Committee of the Fifth Medical Center of Chinese PLA General Hospital (Ethical code: Ky-2018-5-37). These studies were conducted following the Declaration of Helsinki. All subjects provided written informed consent before participation in the present study. The methods of T cell isolation and culture and gene transfer are described in Zhang et al. (2020).

Binding Assay

Briefly, through the measurement of the fluorescence intensity of different CAR T cells to CD19 protein at various concentrations, their affinity for CD19 protein can be determined. Specifically, mock-T, 2nd CAR-T, and 2nd-GG CAR-T cells were washed twice by centrifugation with PBS (1% BSA). They were treated with CD19-Fc protein (11880-H02H) at final concentrations of 180 µg/mL, 72 µg/mL, 28.8 µg/mL, 11.52 µg/mL, 4.61 µg/mL, 1.84 µg/mL, 0.74 µg/mL, 0.29 µg/mL, 0.12 µg/mL, or 0.05 µg/mL, incubated at 4° C. in darkness for 45 min, and washed twice with a PBS washing solution by centrifugation. Next, the cells were treated with 10 µL goat anti-human IgG (FC)/FITC, incubated at 4° C. in darkness for 20 min, washed twice with a washing solution by centrifugation, and tested utilizing flow cytometry (NovoCyte D3010).

Cytotoxicity Assay

Briefly, CFSE-labeled targets were incubated at the indicated ratios with effector T cells for 12-16 h or 6-8 h. The cells were then harvested, and Annexin V and 7-AAD were added prior to flow cytometric analysis. The residual live target cells were $CFSE^+$ Annexin $V^-$ $7\text{-}AAD^-$. E:T ratios designated the ratios of the absolute number of CAR T cells to target cells. The number of T cells was the same as that in the 2nd CAR group. All experiments were carried out in triplicate.

Cytokine Production

Effector cells ($5 \times 10^4$) and target cells ($5 \times 10^4$) were incubated at a 1:1 ratio in RPMI (10% FBS) media with 10% human serum for 24 h. Cytokine concentration in the culture supernatant and mouse serum was measured with enzymelinked immunosorbent assay (ELISA) kits (MultiSciences Biotech Co., Ltd., China) for human IFN-g, TNF-a, and IL-2. E:T ratio designated the ratio of the absolute number of CAR T cells to target cells. The number of T cells was the same as that in the 2nd CAR group.

Flow Cytometry

Anti-human antibodies were purchased from Becton Dickinson, BioLegend, and Miltenyi Biotec. The Accuri C6 (Becton Dickinson, USA), FACS Calibur (Becton Dickinson, USA), and BD FACSAria™ II cell sorter were used for the analysis of various samples. Anti-human antibodies were purchased from BioLegend, eBioscience, Acrobiosystems, or BD. Cells were isolated from in vitro cultures or from animals, washed once with PBS supplemented with 2% FCS, and stained on ice after blocking Fc receptors. In all analyses, the population of interest was gated based on forward vs. side scatter characteristics followed by singlet gating.

Mouse Xenograft Tumor Model

Animal experiments were conducted at the National Beijing Center for Drug Safety Evaluation and Research and at the SAFE Pharmaceutical Research Institute Co., Ltd (IACUC-2019-001). Female NSG mice (28) aged 6-8 weeks were used. For NALM-6-acute precursor B-ALL models, $10^6$ tumor cells were intravenously injected with PBS, and tumors were measured by the total bioluminescent flux using a Xenogen Imaging System (PerkinElmer-IVIS Lumina III). Peripheral blood was collected via the submandibular vein.

Statistical Analysis

Statistical analyses were performed using Prism version 7.0 (GraphPad). For studies comparing two groups, a Students t-test was utilized. Log rank (Mantel Cox) test was used to analyze in vivo survival. Survival curves were constructed using Kaplan-Meier methodology.

Results

Figure 1B:
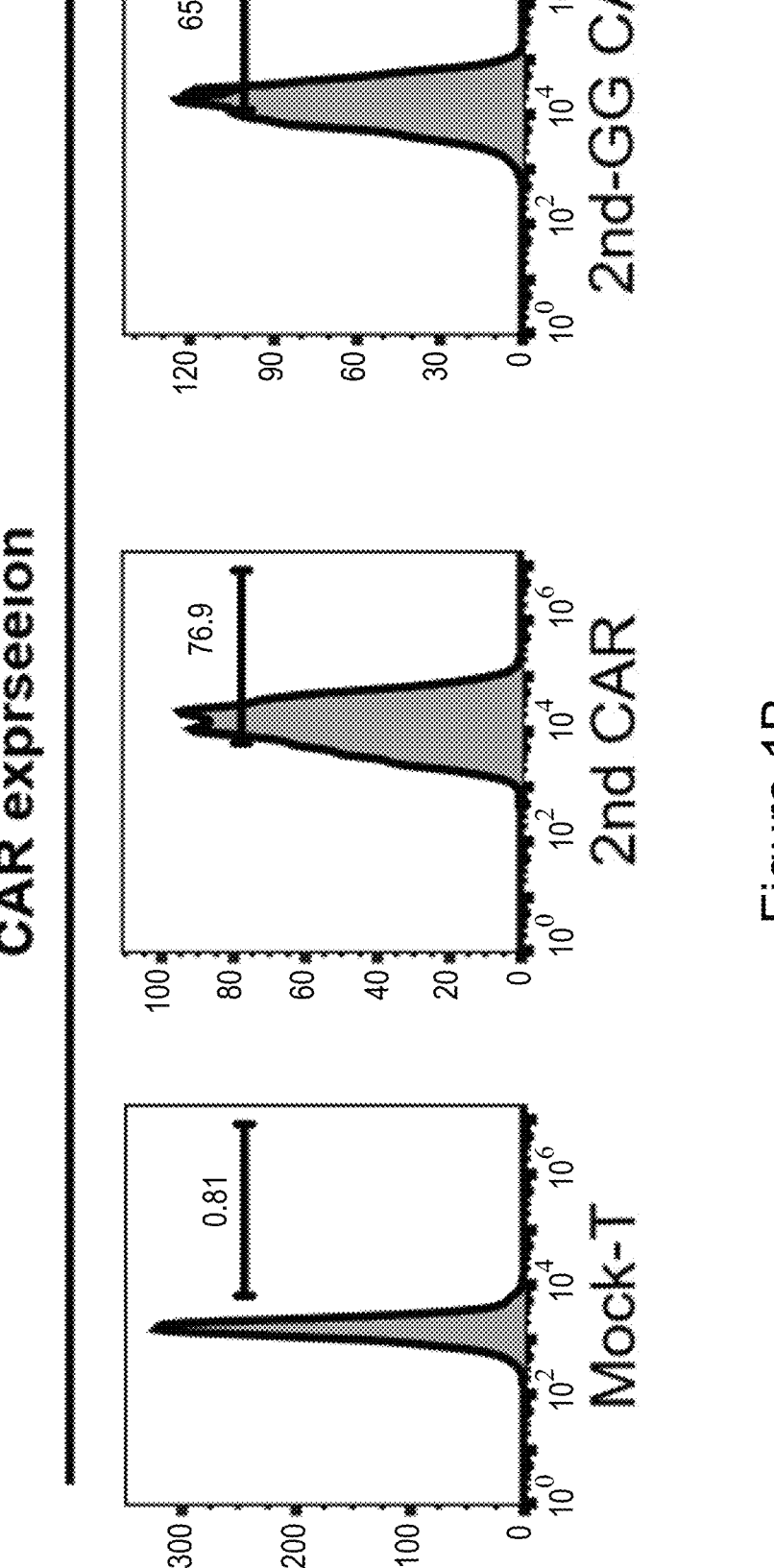
Figure 1C:
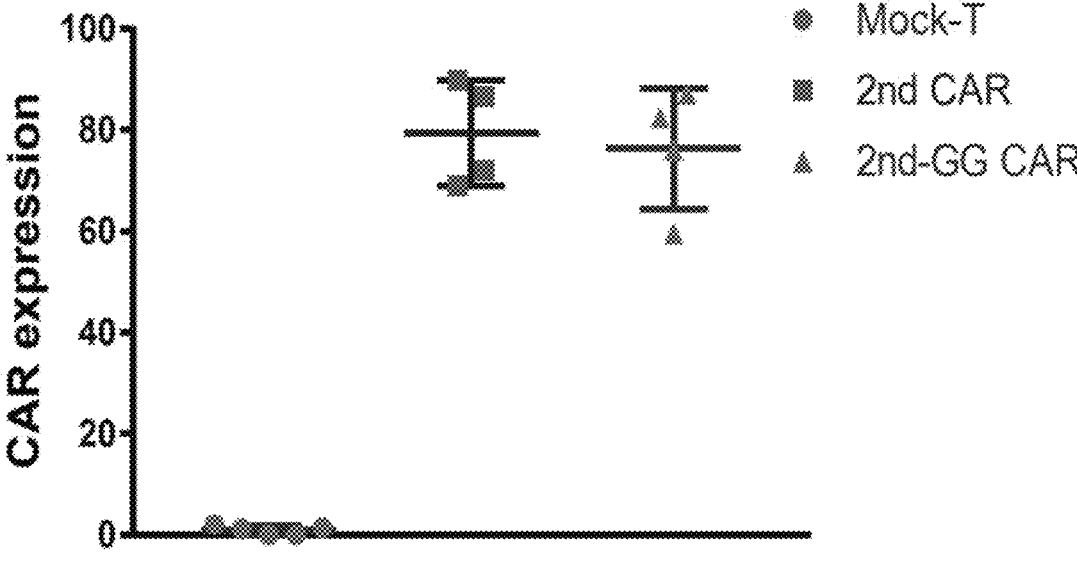
Figure 1D:
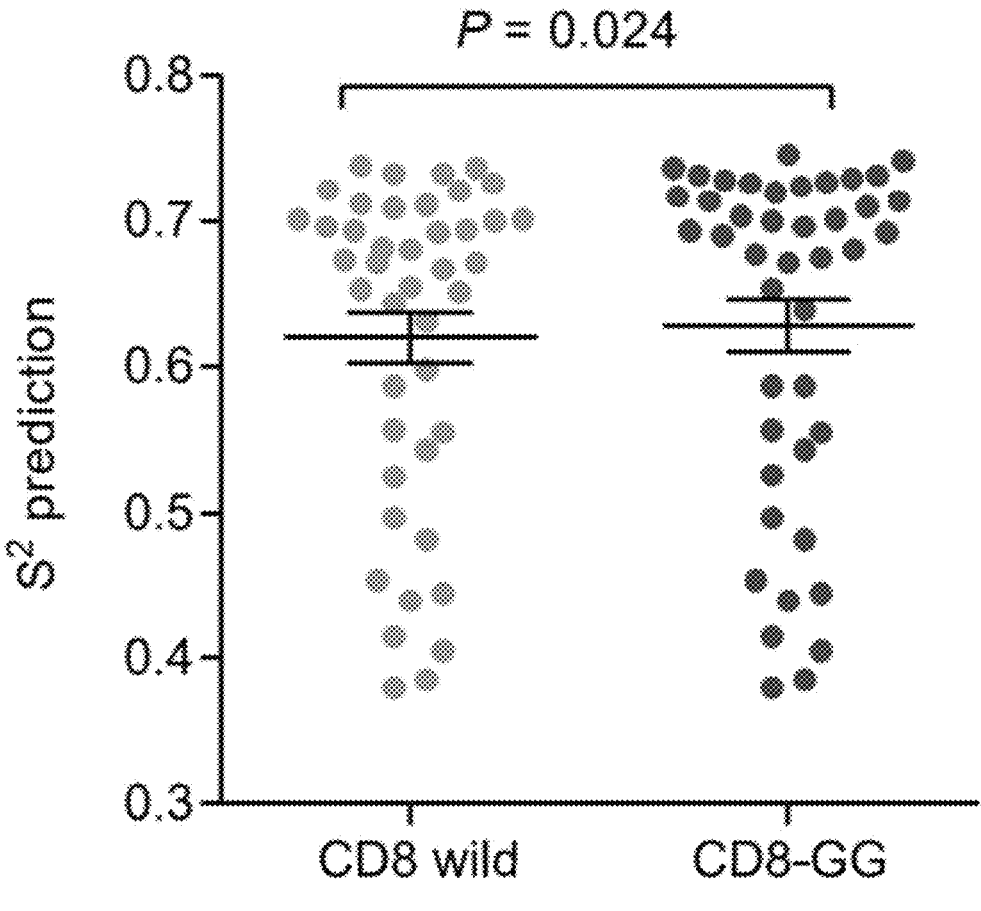
Figure 1E:
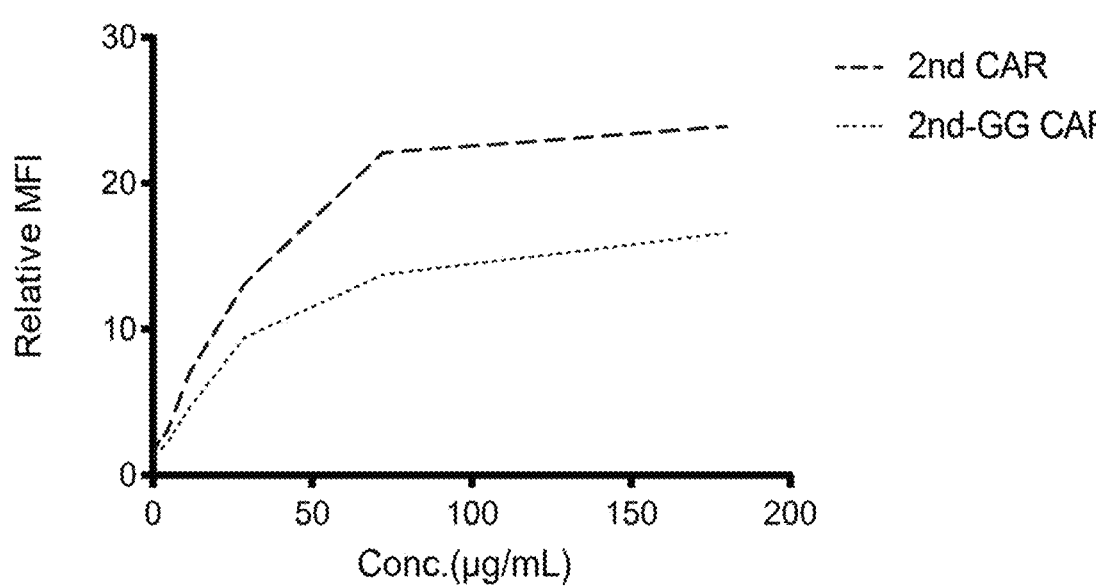

Deletion of Gly-Gly in CD8 Hinge Region of CAR Reduced the Flexibility of Hinge without Affecting the CAR Expression Efficiency The 2nd CAR-T cells, structured as FMC63-CD8-4-1BB-CD3z, have shown promising efficacy in clinical studies. To decrease the flexibility of the hinge region, deletion mutations were performed on two consecutive Glys in the wild-type CD8 hinge region of FMC63-CD8-4-1BB-CD3z CAR, and this novel CAR was named 2nd-GG CAR (FIG. 1A). The transduction efficiency of 2nd CAR and 2nd-GG CAR on human T cells was similar (approximately 70%) (FIGS. 1B, C). The S2 order parameters represent the restriction of movement of an atomic bond vector with respect to the molecular reference frame. The greater the value of S2, the less flexible the protein. Thus, the flexibility of the CD8-GG hinge region was less than that of the CD8 hinge region according to the index of S2 from DynaMine (FIG. 1D). Furthermore, when the two CAR-T cells were individually incubated with different concentrations of CD19 protein, the 2nd-GG CAR-T cells showed weaker binding ability to CD19 protein than 2nd CAR-T cells (FIG. 1E).

Figure 2A:
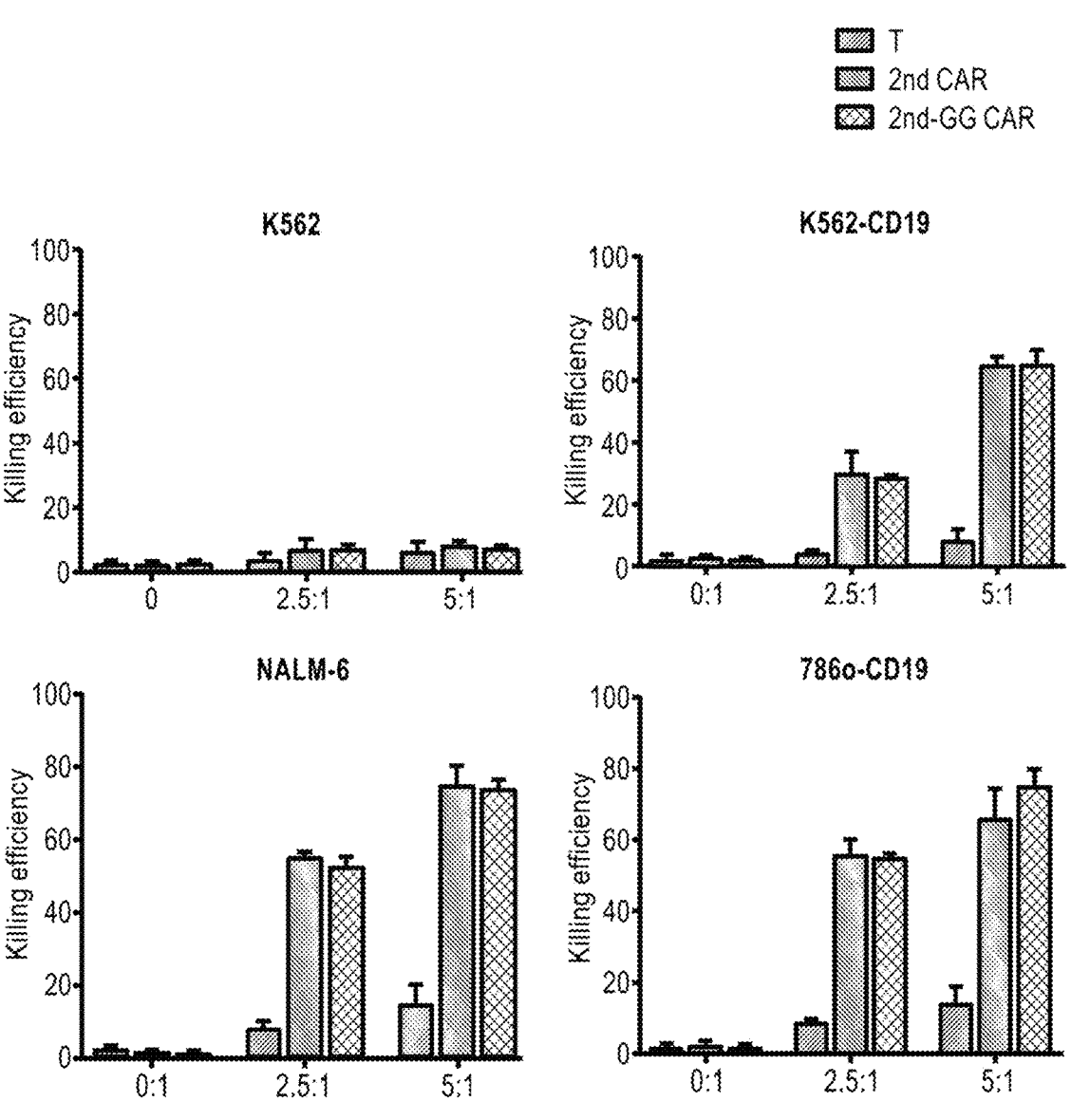
FIGS. 2A-2B show the killing efficiency and cytokine secretion of 2nd CAR-T and 2nd-GG CAR-T cells towards tumor cells.
Figure 2B:
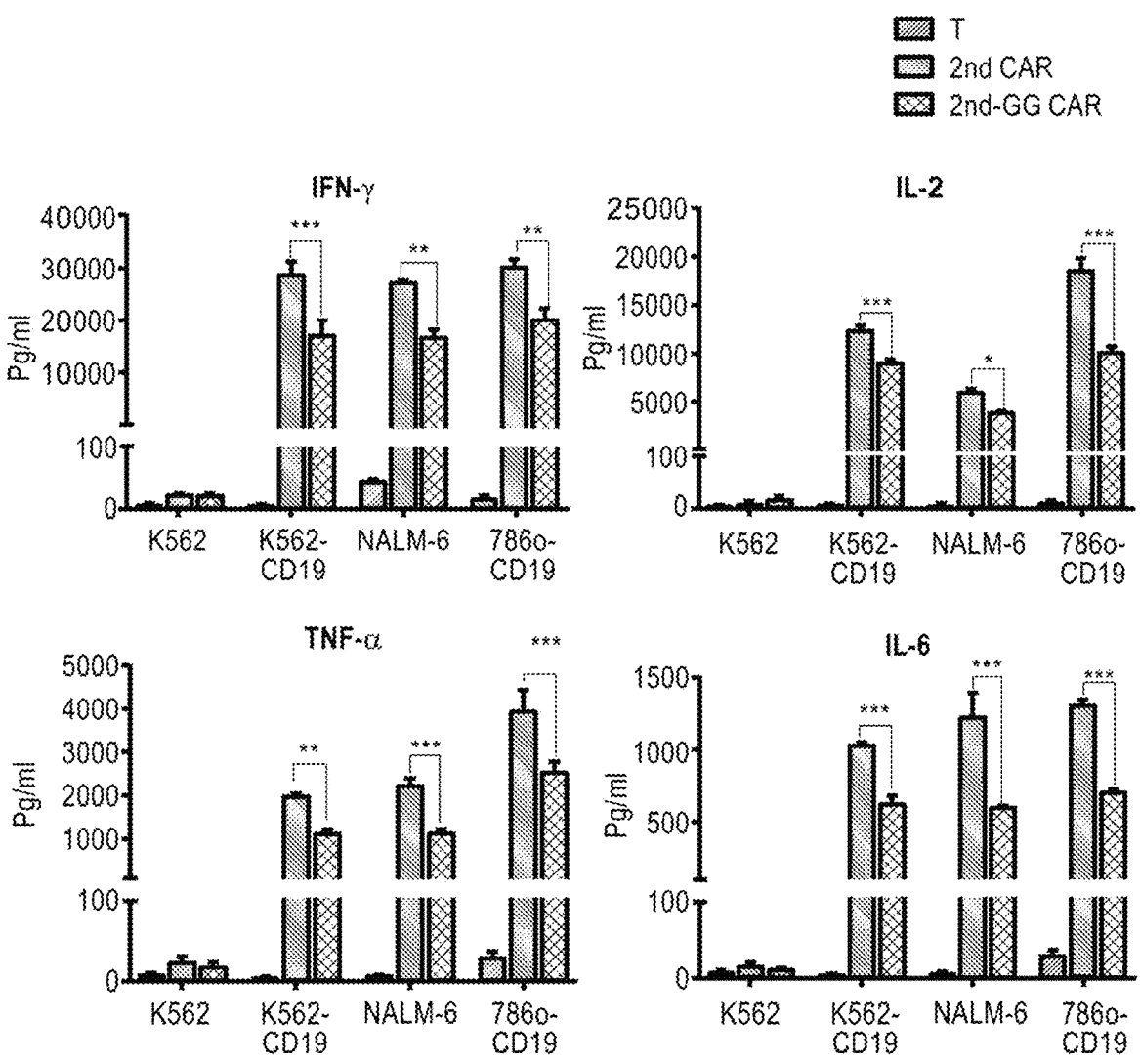

2nd-GG CAR-T Cells Showed Similar Killing Efficiency but Secreted Less Proinflammatory Cytokines To evaluate the effector function of the two different CAR-T cells, a killing (cytotoxicity) and cytokine secretion assays were conducted on different cell lines. These were: NALM-6, a precursor B-cell leukemia cell line that naturally expresses CD19, plus the 786o and K562 cell lines which are CD19 negative (FIG. 2). The two CAR-T cells showed similar cytotoxic efficacy against the CD19-positive and negative cell lines, with no statistically significant differences.

It is well known that cytokines secreted from CAR-T cells trigger an overactivation of the immune system, ultimately leading to cytokine release syndrome (CRS). Therefore release of pro-inflammatory factors after incubation of CAR T cells with different tumor cells was examined. Following incubation with CD19+ target cells, the amount of proinflammatory cytokines secreted by 2nd-GG CAR-T cells was less than that of 2nd CAR-T cells (P<0.01). None of the CART cells produced specific killing effects or proinflammatory factors against K562, a CD19− tumor cell line, demonstrating the antigen specificity towards CD19 by the 2nd-GG CAR-T cells.

Figure 3A:
FIGS. 3A-3E present antitumor efficacy and cytokines release of different CAR-T cells in moderate tumor load models.
Figure 3B:
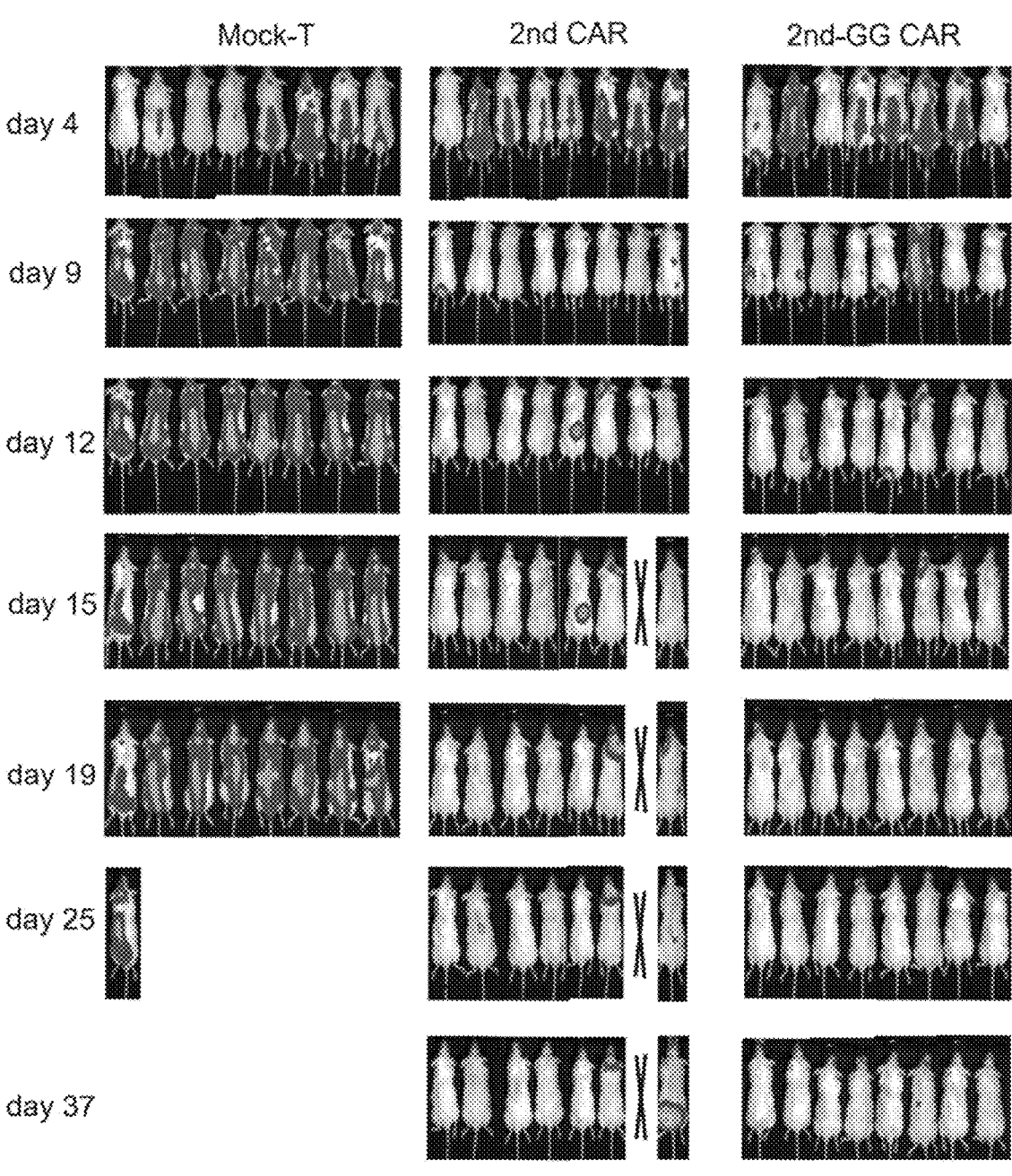
Figure 3C:
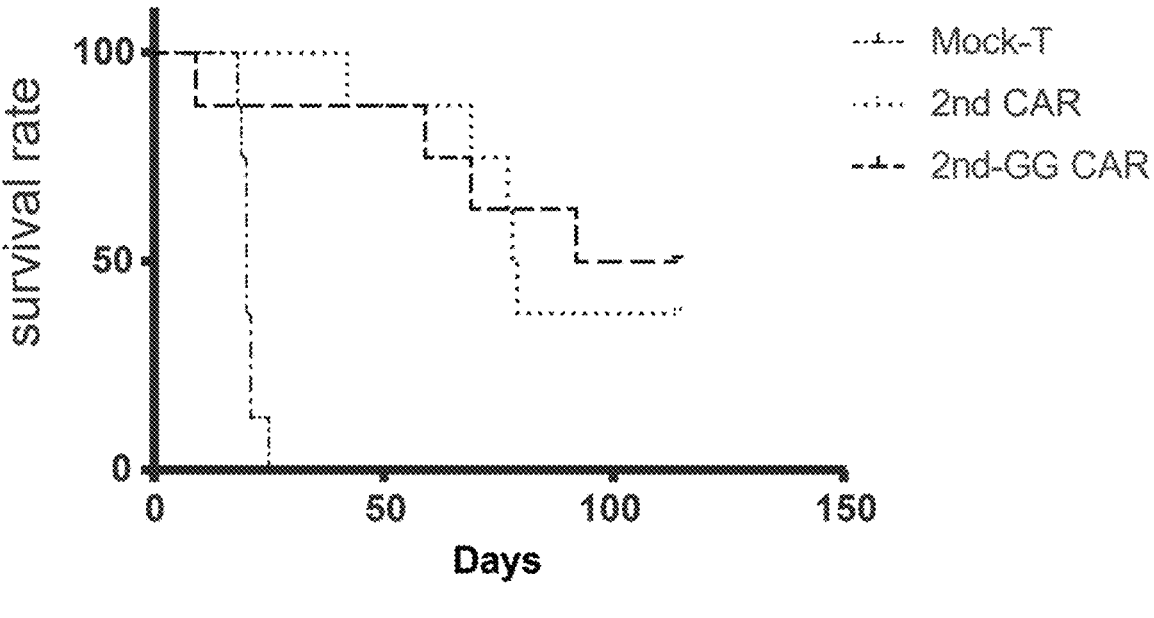
Figure 3D:
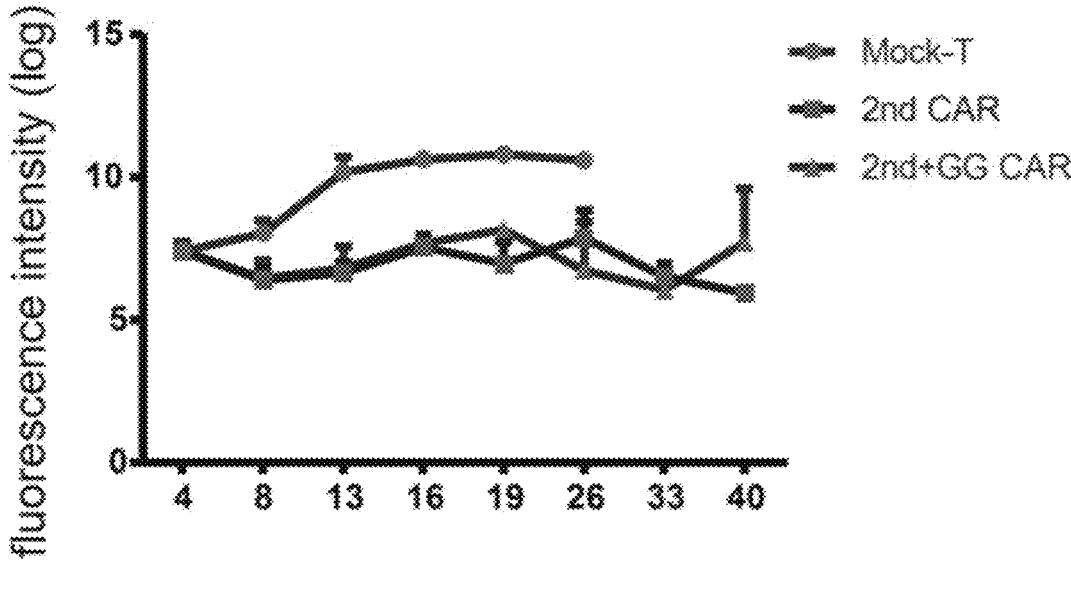
Figure 3E:
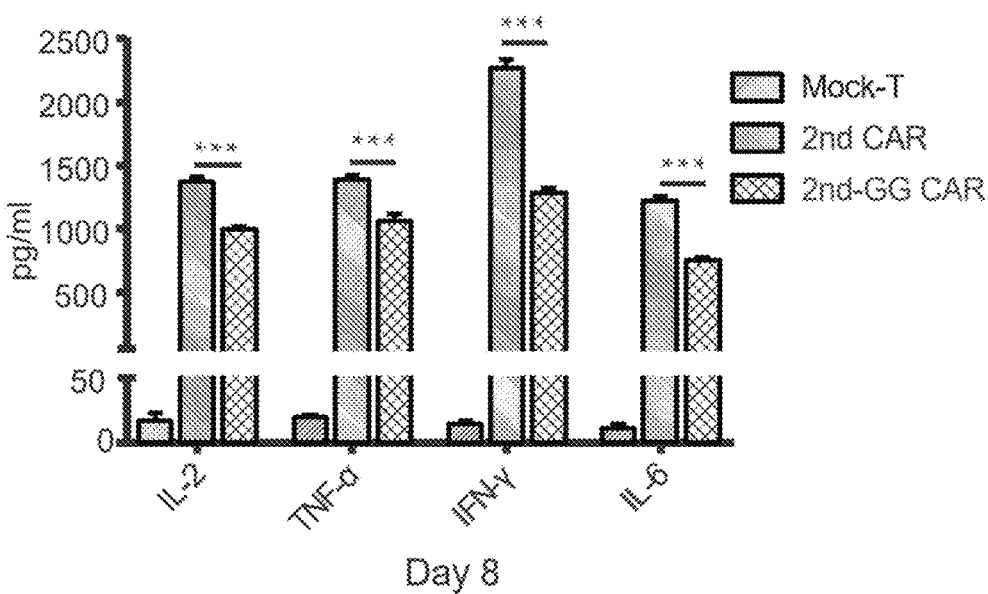

2nd-GG CAR-T Cells Exhibited Similar Antitumor Efficacy but Less Proinflammatory Cytokines Release in Mouse Model with Moderate Tumor Burden Although 2nd-GG CAR-T cells showed a similar specific immune response to CD19+ tumor cells in vitro compared with 2nd CAR T cells, their antitumor efficacy in animal models needs to be further verified. The anti-tumor efficacy of CAR-T cells in NSG immunodeficient mice bearing NALM-6-GFP-luc(luciferase) was subsequently investigated, as detailed in FIG. 3A. Both 2nd-GG and 2nd CAR-T cells exhibited improved overall survival (OS) and reduced tumor burden compared with the mock-T cells, demonstrating improved tumor control of both CAR-T cells (FIGS. 3B, D). Furthermore, compared to the 2nd CAR-T cell group, the OS in those administered 2nd-GG CAR-T cells was prolonged, although there was no statistical difference, as shown in FIG. 3C. As expected, 2nd-GG CAR-T cells secreted less human proinflammatory cytokines, particularly IL-6 and IFN-γ, compared to the 2nd CAR-T cells in vivo (FIG. 3E). In order to distinguish it from the following experiment with a higher tumor burden, this experiment was referred to as "with moderate tumor load". The 2nd-GG CART cells did not show sufficient advantage compared to the 2nd CAR-T cells in experiments with moderate tumor burden, owing to the relatively lower tumor load.

Figures 4A, 4B:
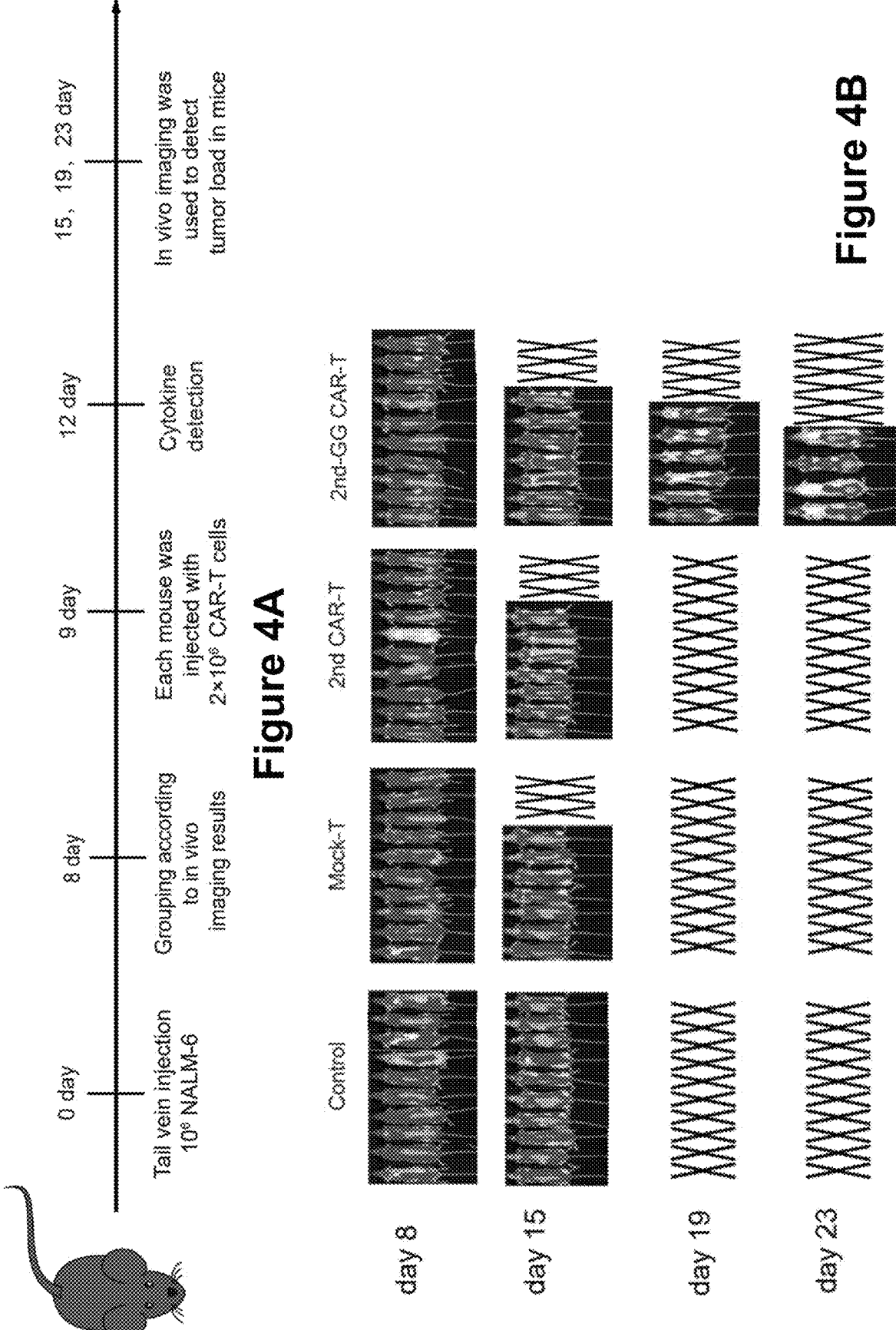
Figure 4C:
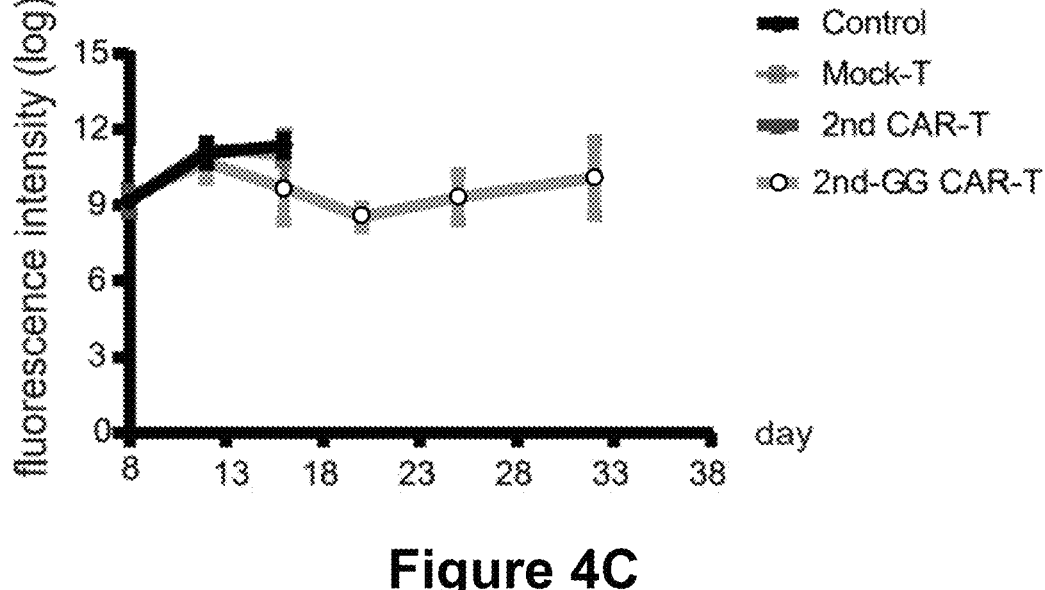
Figure 4D:
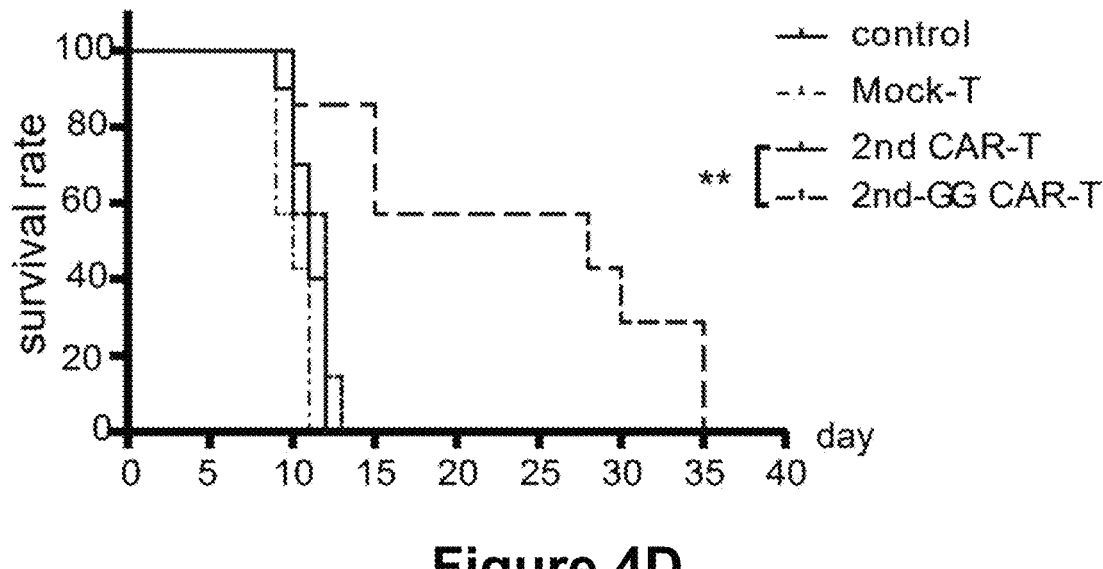
Figure 4E:
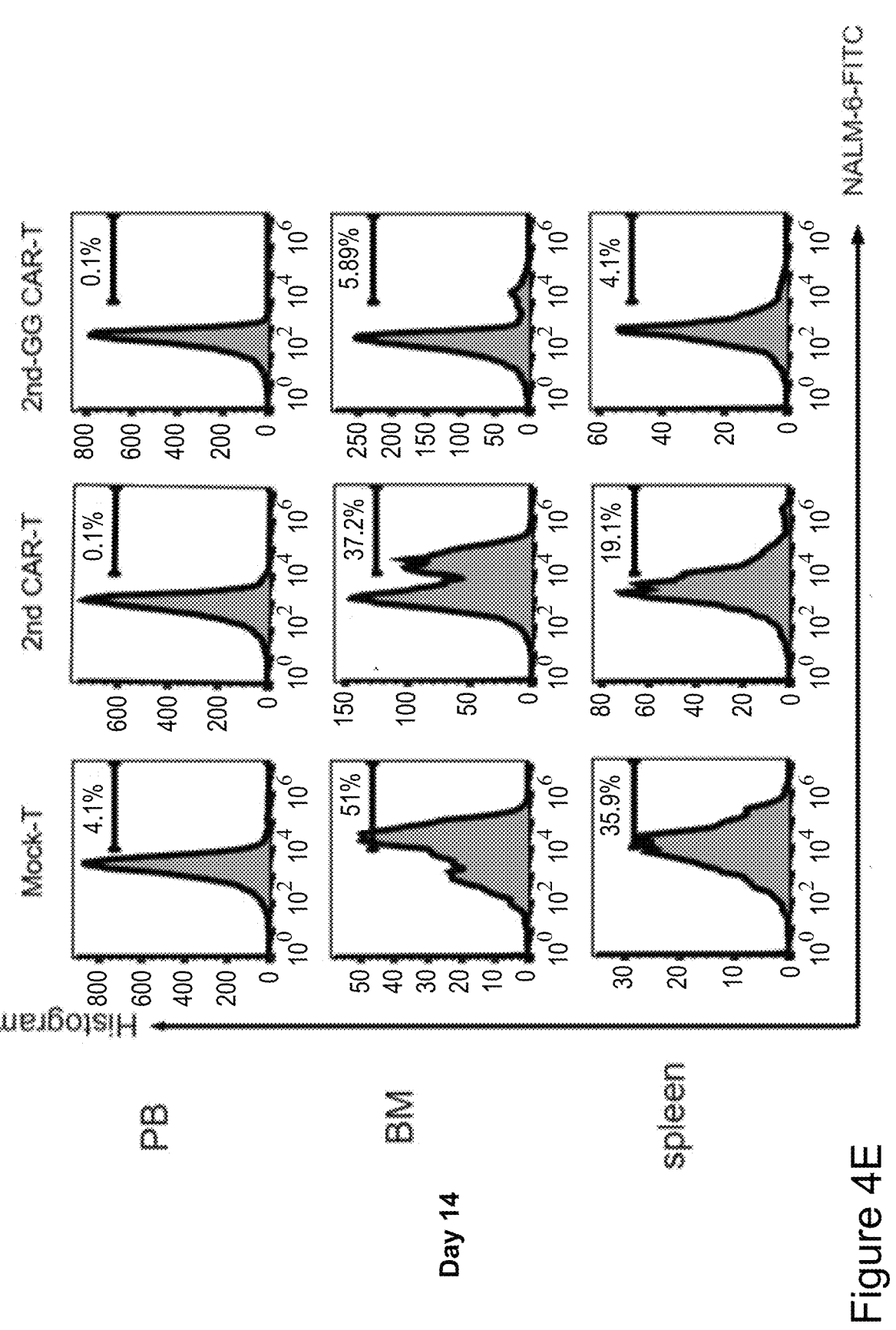
Figure 4F:
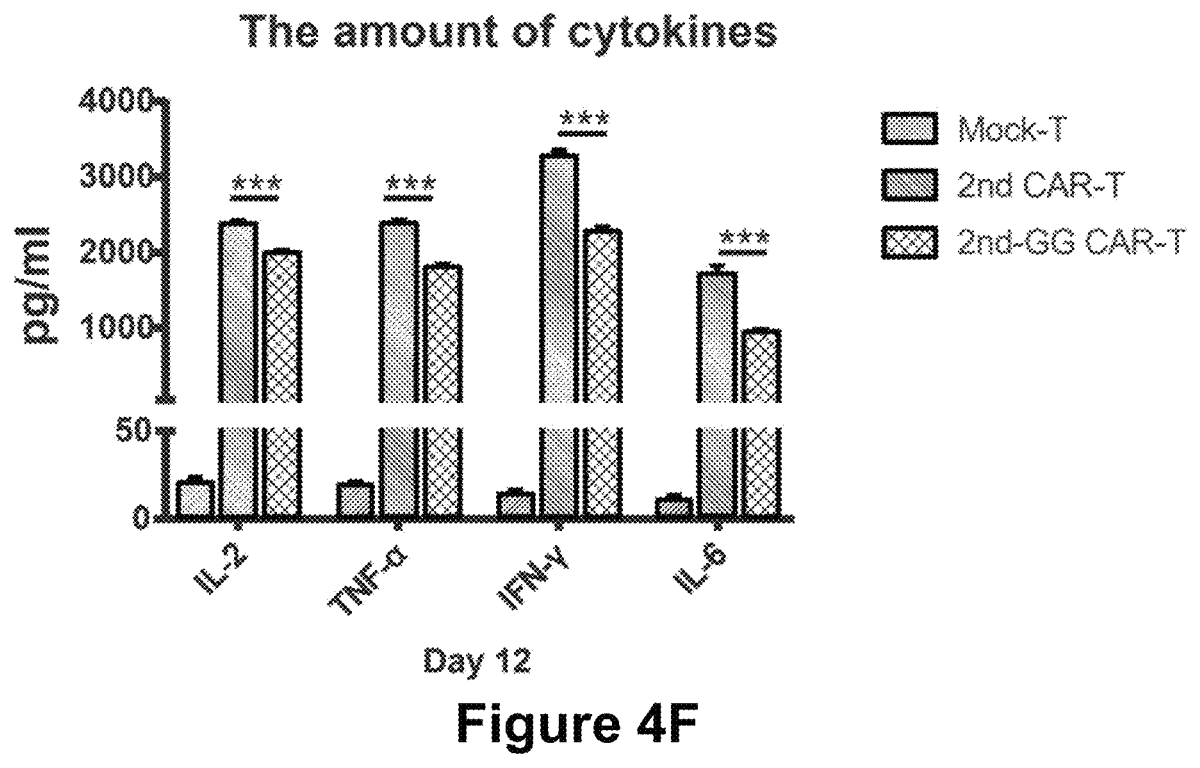

2nd-GG CAR-T Cells Significantly Improved Antitumor Activity in Mouse Model with High Tumor Burden A high tumor burden often indicates a poor prognosis and significant adverse reactions after CAR-T therapy. It is suggested that a high tumor burden might affect the efficacy of CAR-T cell therapy. It was thus hypothesized that CAR T cells behave differently in mouse models with different tumor burdens. To mimic the clinical situation of a high tumor burden, NSG mice bearing NALM6-Luc tumors received delayed CAR-T cell infusion to increase the tumor load. The specific schedule is shown in FIG. 4A. When NSG mice were challenged with high tumor burden, 2nd-GG CAR T cells showed significantly improved overall survival compared with 2nd CAR-T cells, while the 2nd CAR-T cells showed no advantage over the mock-T cells (FIGS. 4B, D). The tumor load in group of 2nd-GG CAR-T was lower than that of 2nd CAR T (P>0.05) on day 15 and showed a downward trend (FIG. 4C). The anergy of 2nd CAR-T cell in the mouse model with high tumor load is likely related to AICD. One mouse from each group was randomly selected on day 14 to evaluate the tumor load of peripheral blood (PB), bone marrow (BM), and spleen by flow cytometry. The results showed that the tumor burden of the 2nd-GG group was less than that of the other two groups after treatment (FIG. 4E). Similarly, the amount of human proinflammatory cytokines secreted by 2nd-GG CAR T cells was lower than that of 2nd CAR T cells (FIG. 4F). Overall, 2nd-GG CAR-T cells exhibited stronger antitumor activity and lower cytokine release in the high tumor burden model than the 2nd CAR-T cells.

Discussion

This study demonstrated that 2nd-GG CAR exhibits lower flexibility and affinity for the CD19 antigen. The 2nd-GG CAR-T cells produced lower levels of cytokines, yet showed similar cytotoxicity to CD19+ tumor cells as 2nd CAR-T cells in vitro. However, 2nd-GG CAR-T cells show lower cytokine release in mouse models with moderate and high tumor burden, and prolong overall survival in animal models with high tumor burden.

Currently, the indication for anti-CD19 CAR T cells has been mainly for relapse and refractory B-cell malignancies, which are often insensitive to traditional radiotherapy and chemotherapy. Furthermore, an inevitable vein-to-vein time interval, typically 3-8 weeks, is required for patients preparing for CAR-T cell therapy. Pivotal trials of approved treatments have resulted in up to a third of the enrolled patients failing to receive the product. It has not been determined if bridging therapy is necessary during this gap, and which treatment regimen may be better. Although off-the-shelf cell therapy or Fast CAR-T cells may shorten the vein-to-vein time interval, it is still under clinical study. Therefore, the high tumor burden in patients before CAR-T cell therapy is an unavoidable problem. It has been reported that both the efficiency and the incidence of adverse reactions, such as CRS of the anti-CD19 second-generation CAR T cells, increased in patients with high tumor burden. Many studies have demonstrated that reduced activation of anti-CD19 CAR-T cells improves the safety and efficiency of CAR-T cells. This could be achieved through reducing anti-CD19 CART cell activation by diminishing scFv affinity, increasing the hinge and transmembrane region, replacing the co-stimulatory molecule from CD28 to 4-1BB, and mutation of the immunoreceptor tyrosine-based activation motif (ITAM) region of CD3ζ.

The hinge region has a significant impact on the function of CAR T cells, and its components are often derived from the IgG family or the co-receptor of T cells (CD4/CD8), but the specific mechanism is still unclear. Studies have shown that the hinge region provides a spatial location for the recognition of scFv and antigens. When the epitope recognized by CAR is in a membrane proximal position, the hinge region is necessary for the recognition of CAR-T cells by antigens, such as when targeting NCAM or 5T4. Whereas if the epitope recognized by CAR is a membrane distal epitope, the hinge region is negligible for the recognition of CAR-T cells by antigens, such as when targeting CEA. In general, little is known about the role of the hinge domain, and strategies to optimize it need to be creatively explored.

The flexibility of the hinge region has been shown to affect the CAR T cell function. It has been reported that addition of a flexible IgG hinge instead of a CD28 hinge alone (SD28ζ) led to more pro-cytokines produce and better recognition of the MUC1 epitope compared to S28ζ CAR-T cells. However, further verification is needed to determine whether reducing the flexibility of the hinge region can decrease CAR-T activity. The present disclosure describes removal of two consecutive glycine residues in the hinge region to reduce the flexibility of the hinge domain, thus resulting in better tumor control and lower release of inflammatory factors such as TNF-α and IL-6, which are the key molecules triggering the cytokine storm. This can be explained by the fact that reducing the flexibility of the hinge domain prevents overactivation of CAR-T cells, especially under high tumor load. Although studies have shown that persistence of CAR-T cells is essential for immune surveillance of tumors, CAR gene copy numbers were unfortunately not measured. Studies have shown that the formation of immune synapses by CAR influences the function of CAR-T cells and changes the flexibility of the hinge region. This may alter the formation of immune synapses in CAR, thus affecting the function of CAR-T cells, though it needs to be further explored.

In the present studies, mice in the group of Mock-T, which had very low level of cytokines, had the highest mortality at day 15. Therefore, the death of mice was not caused by excessive release of cytokines. Recent study demonstrated that patients with high tumor burden had higher immune dysregulation with increased serum inflammatory markers and tumor IFN signaling. IFN signaling is associated with the expression of multiple checkpoint ligands and inferior response to CAR-T therapy. Therefore, it is considered the direct cause of death in high tumor burden model was the increased tumor load. It is hypothesized that lower levels of inflammatory cytokine in vivo improved activity of 2nd-GG CAR-T through correcting the immune dysregulation and reducing tumor IFN signaling.

In summary, the present study demonstrated that a novel CD19 CAR with a less flexible hinge domain showed prolonged survival of mice under high tumor burden in preclinical studies. With potential for improved safety and efficacy, the results presented herein are expected to have beneficial clinical applications.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An isolated chimeric antigen receptor (CAR) molecule comprising an antigen binding domain, a hinge domain, a transmembrane domain, a costimulatory domain, and an intracellular signaling domain, wherein the hinge domain comprising the amino acid sequence of SEQ ID NO: 1.

2. The isolated CAR of claim 1, wherein the hinge domain is encoded by a nucleotide sequence comprising the sequence of SEQ ID NO:2.

3. The isolated CAR of claim 1, wherein the antigen binding domain is a single chain antibody or single chain antibody fragment.

4. The isolated CAR of claim 1, wherein the antigen binding domain binds to a target antigen selected from the group consisting of CD19, CD20, CD22, CD33, CD123, BCMA, CLL1, CD7, CS1, CEA, AFP, PSMA, GPC3, GD2, EGFRVIII, NKG2D, Mesothelin, Claudin 18.2, ROR3, and Muc1.

5. The isolated CAR of claim 1, wherein the antigen binding domain binds to CD19 and comprises a light chain complementary determining region 1 (LC CDR1) having the amino acid sequence of SEQ ID NO:3, a light chain complementary determining region 2 (LC CDR2) having the amino acid sequence of SEQ ID NO:4, a light chain complementary determining region 3 (LC CDR3) having the amino acid sequence of SEQ ID NO:5, and a heavy chain complementary determining region 1 (HC CDR1) having the amino acid sequence of SEQ ID NO:6, a heavy chain complementary determining region 2 (HC CDR2) having the amino acid sequence of SEQ ID NO: 7, and a heavy chain complementary determining region 3 (HC CDR3) having the amino acid sequence of SEQ ID NO: 8.

6. The isolated CAR of claim 1, wherein the antigen binding domain comprises a scFv that binds to CD19, said scFv comprises the amino acid sequence of SEQ ID NO:11.

7. The isolated CAR of claim 1, wherein the transmembrane domain comprises a transmembrane domain of a protein selected from the group consisting of the alpha, beta or zeta chain of T cell receptor, CD28, CD3 epsilon, CD45, CD4, CD5, CD8, CD9, CD16, CD22, CD33, CD37, CD64, CD80, CD86, CD134, CD137 and CD154.

8. The isolated CAR of claim 1, wherein the costimulatory domain comprises a functional signaling domain of a protein selected from the group consisting of OX40, CD2, CD27, CD28, CDS, ICAM-1, LFA-1 (CD11a/CD18), ICOS (CD278), and 4-1BB (CD137).

9. The isolated CAR of claim 1, wherein the intracellular signaling domain comprises an intracellular signaling domain of CD3 zeta, or FcR gamma, or a functional fragment thereof.

10. A nucleic acid construct comprising one or more nucleic acid sequences, said nucleic acid sequences encode the isolated CAR of claim 1.

11. An expression vector comprising the nucleic acid construct of claim 10.

12. A cell comprising the expression vector of claim 11.

13. The cell of claim 12, wherein the cell is an immune cell.

14. The cell of claim 13, wherein the immune cell is a T cell.

15. A composition comprising the cell of claim 12 and a pharmaceutically acceptable carrier.

* * * * *